US010200798B2

(12) United States Patent
Crawford et al.

(10) Patent No.: US 10,200,798 B2
(45) Date of Patent: *Feb. 5, 2019

(54) COCHLEAR IMPLANT HEADPIECE

(71) Applicant: Advanced Bionics AG, Staefa (CH)

(72) Inventors: Scott A. Crawford, Castaic, CA (US); Douglas P. Lynch, Shepherdstown, WV (US); Carla Mann Woods, Beverly Hills, CA (US); Glen A. Griffith, Newbury Park, CA (US)

(73) Assignee: Advanced Bionics AG, Staefa (CH)

( * ) Notice: Subject to any disclaimer, the term of this patent is extended or adjusted under 35 U.S.C. 154(b) by 32 days.

This patent is subject to a terminal disclaimer.

(21) Appl. No.: 15/206,124

(22) Filed: Jul. 8, 2016

(65) Prior Publication Data
US 2016/0317810 A1 Nov. 3, 2016

Related U.S. Application Data

(63) Continuation of application No. 14/308,591, filed on Jun. 18, 2014, now Pat. No. 9,392,384, which is a (Continued)

(51) Int. Cl.
*H04R 25/00* (2006.01)
*A61N 1/378* (2006.01)
(Continued)

(52) U.S. Cl.
CPC ....... *H04R 25/554* (2013.01); *A61N 1/36036* (2017.08); *A61N 1/3787* (2013.01);
(Continued)

(58) Field of Classification Search
CPC ............ A61N 1/36032; A61N 1/36036; A61N 1/37229; A61N 1/3787; H04R 25/602;
(Continued)

(56) References Cited

U.S. PATENT DOCUMENTS 2,975,226 A    3/1961 Lehr
3,055,990 A    9/1962 Sildo
(Continued)

FOREIGN PATENT DOCUMENTS

WO    WO 9837926 A1    9/1998
WO    WO 0001442 A2    1/2000
(Continued)

OTHER PUBLICATIONS

"Adjustable Strength Magnet System for a Cochlear Implant Headpiece"; IP.com Publication; IPCOMOOO010043D; (Oct. 2002).
(Continued)

*Primary Examiner* — Oyesola C Ojo
(74) *Attorney, Agent, or Firm* — Henricks Slavin LLP

(57) ABSTRACT

A headpiece for use with a cochlear implant including a headpiece housing, a retention magnet within the headpiece housing that generates a retention magnetic field, the retention magnet including a bottom surface that faces the cochlear implant, a top surface opposite the bottom surface, and an outer radial surface between the top and bottom surfaces, an induction coil within the headpiece housing that transmits audio signals to the cochlear implant by generating a telemetry magnetic field, and a retention flux guide within the headpiece housing and adjacent to the top surface of the retention magnet.

26 Claims, 13 Drawing Sheets

Related U.S. Application Data continuation of application No. 12/398,058, filed on Mar. 4, 2009, now Pat. No. 8,811,643, which is a continuation of application No. 10/823,880, filed on Apr. 14, 2004, now Pat. No. 7,599,508.

(60) Provisional application No. 61/113,675, filed on Nov. 12, 2008, provisional application No. 60/469,082, filed on May 8, 2003.

(51) Int. Cl.
*A61N 1/372* (2006.01)
*A61N 1/36* (2006.01)

(52) U.S. Cl.
CPC ......... *A61N 1/37229* (2013.01); *H04R 25/00* (2013.01); *H04R 25/602* (2013.01); *H04R 25/604* (2013.01); *H04R 25/652* (2013.01); *H04R 2225/021* (2013.01)

(58) Field of Classification Search
CPC .. H04R 25/554; H04R 25/604; H04R 25/652; H04R 25/00; H04R 2225/021
See application file for complete search history.

(56) References Cited

U.S. PATENT DOCUMENTS

| | | | | |
|---|---|---|---|---|
| 3,942,535 | A | 3/1976 | Schulman | |
| 4,006,748 | A | 2/1977 | Schulman | |
| 4,041,955 | A | 8/1977 | Kelly et al. | |
| 4,134,408 | A | 1/1979 | Brownlee | |
| 4,352,960 | A | 10/1982 | Dormer et al. | |
| 4,379,988 | A | 4/1983 | Mattatall | |
| 4,532,930 | A | 8/1985 | Crosby et al. | |
| 4,592,359 | A | 6/1986 | Galbraith | |
| 4,819,647 | A * | 4/1989 | Byers | A61N 1/0541 128/903 |
| RE32,947 | E | 6/1989 | Dormer et al. | |
| 4,918,736 | A | 4/1990 | Bordewijk et al. | |
| 4,947,439 | A | 8/1990 | Buettner | |
| 5,095,904 | A * | 3/1992 | Seligman | A61N 1/36036 607/57 |
| 5,126,663 | A * | 6/1992 | Shinjo | G01D 5/147 123/617 |
| 5,279,292 | A | 1/1994 | Baumann et al. | |
| 5,313,053 | A * | 5/1994 | Koenck | B60R 11/02 235/470 |
| 5,314,451 | A | 5/1994 | Mulier | |
| 5,411,537 | A | 5/1995 | Munshi et al. | |
| 5,411,538 | A | 5/1995 | Lin | |
| 5,522,865 | A | 6/1996 | Schulman et al. | |
| 5,571,148 | A * | 11/1996 | Loeb | A61N 1/36036 607/55 |
| 5,603,726 | A | 2/1997 | Schulman et al. | |
| 5,610,494 | A | 3/1997 | Grosfilley | |
| 5,625,699 | A * | 4/1997 | Yamada | H04R 3/14 381/412 |
| 5,626,629 | A | 5/1997 | Faltys et al. | |
| 5,702,431 | A | 12/1997 | Wang et al. | |
| 5,737,430 | A * | 4/1998 | Widrow | H04R 25/407 381/312 |
| 5,749,912 | A * | 5/1998 | Zhang | A61N 1/36036 607/55 |
| 5,793,875 | A * | 8/1998 | Lehr | H04R 25/554 381/313 |
| 5,824,022 | A | 10/1998 | Zilberman et al. | |
| 5,906,635 | A | 5/1999 | Maniglia | |
| 5,948,006 | A | 9/1999 | Mann | |
| 5,949,895 | A | 9/1999 | Ball et al. | |
| 6,051,017 | A | 4/2000 | Loeb et al. | |
| 6,067,474 | A * | 5/2000 | Schulman | A61N 1/08 607/57 |
| 6,129,753 | A | 10/2000 | Kuzma et al. | |
| 6,190,305 | B1 | 2/2001 | Ball et al. | |
| 6,218,753 | B1 * | 4/2001 | Asano | H02K 1/276 310/156.53 |
| 6,219,580 | B1 * | 4/2001 | Faltys | A61N 1/36036 607/57 |
| 6,246,911 | B1 | 6/2001 | Seligman | |
| 6,249,704 | B1 | 6/2001 | Maltan et al. | |
| 6,265,100 | B1 | 7/2001 | Saaski et al. | |
| 6,272,382 | B1 * | 8/2001 | Faltys | A61N 1/08 607/57 |
| 6,275,736 | B1 | 8/2001 | Kuzma et al. | |
| 6,275,737 | B1 | 8/2001 | Mann | |
| 6,289,247 | B1 | 9/2001 | Faltys et al. | |
| 6,304,787 | B1 | 10/2001 | Kuzma et al. | |
| 6,308,101 | B1 * | 10/2001 | Faltys | A61N 1/08 607/57 |
| 6,310,960 | B1 | 10/2001 | Saaski et al. | |
| 6,324,431 | B1 | 11/2001 | Zarinetchi | |
| 6,358,281 | B1 | 3/2002 | Berrang et al. | |
| 6,389,318 | B1 * | 5/2002 | Zarinetchi | A61N 1/3787 607/60 |
| 6,394,947 | B1 | 5/2002 | Leysieffer | |
| 6,415,185 | B1 | 7/2002 | Maltan | |
| 6,434,429 | B1 | 8/2002 | Kraus et al. | |
| 6,473,511 | B1 | 10/2002 | Aceti et al. | |
| 6,496,734 | B1 | 12/2002 | Money | |
| 6,556,870 | B2 | 4/2003 | Zierhofer et al. | |
| 6,560,488 | B1 | 5/2003 | Crawford | |
| 6,648,914 | B2 | 11/2003 | Berrang et al. | |
| 6,658,124 | B1 | 12/2003 | Meadows | |
| 6,671,559 | B2 * | 12/2003 | Goldsmith | A61N 1/36036 607/57 |
| 6,726,618 | B2 | 4/2004 | Miller | |
| 6,786,860 | B2 | 9/2004 | Maltan et al. | |
| 6,807,445 | B2 | 10/2004 | Baumann et al. | |
| 6,838,963 | B2 * | 1/2005 | Zimmerling | A61N 1/37 335/205 |
| 6,842,647 | B1 | 1/2005 | Griffith | |
| 6,850,803 | B1 | 2/2005 | Jimenez et al. | |
| 6,862,805 | B1 | 3/2005 | Kuzma et al. | |
| 6,879,695 | B2 | 4/2005 | Maltan | |
| 6,879,855 | B2 | 4/2005 | Schulman et al. | |
| 7,043,303 | B1 | 5/2006 | Overstreet | |
| 7,054,691 | B1 | 5/2006 | Kuzma et al. | |
| 7,120,501 | B2 * | 10/2006 | Boylston | A61N 1/36036 607/57 |
| 7,149,551 | B2 | 12/2006 | Kim | |
| 7,174,214 | B2 | 2/2007 | Seligman | |
| 7,266,208 | B2 | 9/2007 | Charvin et al. | |
| 7,266,209 | B1 * | 9/2007 | House | A61N 1/36036 381/312 |
| 7,292,880 | B2 | 11/2007 | Lehtonen | |
| 7,349,741 | B2 | 3/2008 | Maltan et al. | |
| 7,386,143 | B2 | 6/2008 | Easter et al. | |
| 7,505,816 | B2 | 3/2009 | Schmeling et al. | |
| 7,599,508 | B1 | 10/2009 | Lynch et al. | |
| 7,848,817 | B2 * | 12/2010 | Janzig | A61N 1/3605 607/45 |
| 7,945,334 | B2 | 5/2011 | Jimenez et al. | |
| 8,013,699 | B2 | 9/2011 | Zimmerling | |
| 8,107,661 | B1 | 1/2012 | Lynch et al. | |
| 8,170,253 | B1 | 5/2012 | Lynch et al. | |
| 8,270,647 | B2 | 9/2012 | Crawford et al. | |
| 8,280,524 | B2 | 10/2012 | Duftner et al. | |
| 8,515,112 | B2 | 8/2013 | Crawford et al. | |
| 8,583,246 | B2 * | 11/2013 | Money | A61N 1/36036 607/57 |
| 8,811,643 | B2 | 8/2014 | Crawford et al. | |
| 8,897,883 | B2 | 11/2014 | Griffith | |
| 8,983,102 | B2 | 3/2015 | Crawford et al. | |
| 9,392,384 | B2 | 7/2016 | Crawford et al. | |
| 9,674,620 | B2 | 6/2017 | Crawford et al. | |
| 2002/0019669 | A1 * | 2/2002 | Berrang | A61N 1/36036 623/10 |
| 2002/0032472 | A1 * | 3/2002 | Zarinetchi | A61N 1/3787 607/61 |
| 2002/0076071 | A1 | 6/2002 | Single | |

(56) References Cited

U.S. PATENT DOCUMENTS

| | | | |
|---|---|---|---|
| 2002/0120332 A1* | 8/2002 | Law | A61N 1/0526 623/11.11 |
| 2003/0011359 A1* | 1/2003 | Ashe | A61B 5/06 324/207.17 |
| 2003/0086583 A1 | 5/2003 | Maltan et al. | |
| 2003/0098669 A1 | 5/2003 | Hensel | |
| 2003/0167077 A1* | 9/2003 | Blamey | A61N 1/36036 607/57 |
| 2004/0044389 A1 | 3/2004 | Crawford | |
| 2004/0073275 A1 | 4/2004 | Maltan et al. | |
| 2004/0133065 A1 | 7/2004 | Easter et al. | |
| 2004/0172102 A1 | 9/2004 | Leysieffer | |
| 2004/0202339 A1 | 10/2004 | O'Brien, Jr. et al. | |
| 2004/0249428 A1* | 12/2004 | Wang | A61F 2/90 607/116 |
| 2005/0004629 A1 | 1/2005 | Gibson et al. | |
| 2005/0113888 A1* | 5/2005 | Jimenez | A61N 1/3787 607/61 |
| 2005/0159791 A1 | 7/2005 | Daly et al. | |
| 2005/0245991 A1 | 11/2005 | Faltys et al. | |
| 2005/0251225 A1 | 11/2005 | Faltys et al. | |
| 2005/0267549 A1* | 12/2005 | Della Santina | A61N 1/372 607/57 |
| 2006/0015155 A1 | 1/2006 | Charvin | |
| 2006/0052841 A1 | 3/2006 | Daly et al. | |
| 2006/0184212 A1 | 8/2006 | Faltys et al. | |
| 2006/0190059 A1 | 8/2006 | Griffith | |
| 2007/0053534 A1 | 3/2007 | Kiratzidis | |
| 2007/0055321 A1 | 3/2007 | Gordon et al. | |
| 2007/0104342 A1 | 5/2007 | Seligman | |
| 2007/0106345 A1 | 5/2007 | Seligman | |
| 2007/0191673 A1 | 8/2007 | Ball et al. | |
| 2007/0282394 A1 | 12/2007 | Segel et al. | |
| 2008/0002834 A1 | 1/2008 | Hochmair | |
| 2008/0205680 A1 | 8/2008 | Ho et al. | |
| 2008/0228243 A1 | 9/2008 | Maltan et al. | |
| 2009/0005836 A1 | 1/2009 | Chang et al. | |
| 2009/0177247 A1 | 7/2009 | Neal et al. | |
| 2010/0036458 A1 | 2/2010 | Duftner et al. | |
| 2010/0046778 A1 | 2/2010 | Crawford et al. | |
| 2010/0046779 A1 | 2/2010 | Crawford et al. | |
| 2011/0009924 A1* | 1/2011 | Meskens | A61N 1/36032 607/57 |
| 2011/0224789 A1 | 9/2011 | Griffith | |
| 2011/0234155 A1 | 9/2011 | Chen et al. | |
| 2011/0264172 A1 | 10/2011 | Zimmerling et al. | |
| 2013/0116747 A1 | 5/2013 | Crawford et al. | |
| 2013/0261701 A1* | 10/2013 | Kuratle | A61N 1/0541 607/57 |
| 2015/0012058 A1 | 1/2015 | Crawford et al. | |
| 2015/0045855 A1 | 2/2015 | Griffith | |
| 2015/0265842 A1* | 9/2015 | Ridler | A61N 1/37229 607/57 |

FOREIGN PATENT DOCUMENTS

| | | |
|---|---|---|
| WO | WO 0139830 A2 | 6/2001 |
| WO | WO 0150816 A1 | 7/2001 |
| WO | WO 03030772 A2 | 4/2003 |
| WO | WO 03/081976 A2 | 10/2003 |
| WO | WO 2005062668 A | 7/2005 |
| WO | WO 2005110530 A2 | 11/2005 |
| WO | WO 2007124325 A2 | 11/2007 |
| WO | WO 2007146773 A1 | 12/2007 |
| WO | WO 2008010647 A1 | 1/2008 |
| WO | WO 2010017118 A1 | 2/2010 |
| WO | WO 2010056751 A1 | 5/2010 |
| WO | WO 2010056768 A1 | 5/2010 |
| WO | WO 2010056770 A1 | 5/2010 |

OTHER PUBLICATIONS

JABRA Corporation; "JABRA FreeSpeak(tm) BT200 Wireless Mobile Headset Users Manual"; JABRA Corporation of 9171 Towne Centre Drive, Suite 500, San Diego, California 92122; (2004); http://www.wirelessgalaxy.comfacfjabra/BTFS_Manual.pdf.

Qian, et al.; "A Bluetooth-Based Wireless Phone Adapter for Cochlear Implant Users"; Department of Electrical Engineering University of Texas at Dallas; http://www.utdallas.edu/~loizou/cimplants/bluetooth.pdf; Asilomar (2001).

Qian, et al.; "A Phone-Assistive Device Based on Bluetooth Technology for Cochlear Implant Users"; IEEE Transactions on Neural Systems and Rehabilitation Engineering; (Jan. 2003); pp. 282-287.

Cap. (n.d.); Webster's New Milennium™ Dictionary of English, Preview Edition (v 0.9.7); Retrieved Jan. 21, 2009; from Dictionary.com website: http://dictionary.reference.com/browse/cap.

Cap; Retrieved Jan. 21, 2009; from http://www.yourdictionary.com/cap.

Cap; (2009); In Merriam-Webster Online Dictionary; Retrieved Jan. 21, 2009; from http://www.merriam-webster.Comfdictionary/cap.

BionicEar.com—Harmony Cochlear Implant by Advanced Bionics; "Components of a Cochlear Implant".

Welcome to Spokane Ear, Nose & Throat Clinic, P.S. Surgery Center; Retrieved Jan. 20, 2009; from http://WWW.spokaneent.com/cochlear_implants.html.

Cochlear Implant; Medical Articles of Interest from Garamchai.Com; Retrieved Jan. 20, 2009; from http://WWW.garamchai.com/DesiTrendsMedical1.htm.

Cochlear Implant Programme; Cochlear Implants, Speech Laboratory, Audiology, E . . . ; Retrieved Jan. 20, 2009; from http://WWW.kkrenthospital.org/surgery_cochlear.htm.

"Cochlear Implants Bring Identity Change"; Otolaryngology—Head and Neck Surgery; Breakthrough; Autumn 2004; p. 6.

UCSF—Cochlear Implant; "Implant System"; Retrieved Jan. 20, 2009; from http://cochlearimplant.ucsf.edu/page.asp?bodyid=implantsystem.

"Cochlear Implants and Children"; Advance for Audiologists; Sep./Oct. 2000; p. 26; WWW.advanceforAUD.com.

Cochlear implants—What is a Cochlear Implant and How Does it Work?; My Baby's Hearing; Retrieved Jan. 20, 2009; from http://WWW.babyhearing.org/HearingAmplification/Cochlear/whathow.asp.

House, William F.; "The All Hear Cochlear Implant System: the AliHear Device, their Manufacture, Preliminary Test Results, & the Future"; p. 1-46; Retrieved Mar. 3, 2009; from http://WWW.allhear.com/pdf/allhear_system.pdf.

Hansaton Akustik Gmbh, Product Brochures and Technical Information; Stueckenstrasse 48-D-22081, Hamburg, Germany, W'NW.hansaton.de (2001-2002).

Florian, John. "Technologically, cochlear implants have taken giant steps." *The Hearing Journal* vol. 56, No. 4 (Apr. 2003) pp. 48.55.

* cited by examiner

COCHLEAR IMPLANT HEADPIECE

CROSS-REFERENCE TO RELATED APPLICATIONS

The present application is a continuation of U.S. application Ser. No. 14/308,591, filed Jun. 18, 2014, now U.S. Pat. No. 9,392,384, which is a continuation of U.S. application Ser. No. 12/398,058, filed Mar. 4, 2009, now U.S. Pat. No. 8,811,643, which claims priority under 35 U.S.C. § 119(e) to U.S. Provisional Application No. 61/113,675, by Scott A. Crawford et al., filed on Nov. 12, 2008, and entitled "Integrated Cochlear Implant Headpiece," which application is hereby incorporated by reference in its entirety. U.S. application Ser. No. 12/398,058 is also a continuation-in-part, and claims the benefit under 35 U.S.C. § 120, of U.S. application Ser. No. 10/823,880, filed Apr. 14, 2004, now U.S. Pat. No. 7,599,508, which claims the benefit under 35 U.S.C. § 119(e) of U.S. Provisional Application No. 60/469,082, filed May 8, 2003. These applications are hereby incorporated by reference in their entireties.

Additionally, filed on the same day as U.S. application Ser. No. 12/398,058 and entitled "Modular Speech Processor" is hereby incorporated by reference in its entirety.

BACKGROUND

In human hearing, hair cells in the cochlea respond to sound waves and produce corresponding auditory nerve impulses. These nerve impulses are then conducted to the brain and perceived as sound.

Hearing loss, which may be due to many different causes, is generally of two types: conductive and sensorineural. Conductive hearing loss typically occurs where the normal mechanical pathways for sound to reach the hair cells in the cochlea are impeded, for example, from damage to the ossicles. Conductive hearing loss may often be helped by using conventional hearing aids that amplify sounds so that acoustic information can reach the cochlea and the hair cells. Some types of conductive hearing loss are also amenable to alleviation by surgical procedures.

Many people who are profoundly deaf, however, have sensorineural hearing loss. This type of hearing loss can arise from the absence or the destruction of the hair cells in the cochlea which then no longer transduce acoustic signals into auditory nerve impulses. Individuals with sensorineural hearing loss may be unable to derive any meaningful benefit from conventional hearing aid systems no matter how loud the acoustic stimulus is. This is because the mechanism for transducing sound energy into auditory nerve impulses has been damaged. Thus, in the absence of properly functioning hair cells, auditory nerve impulses cannot be generated directly from sounds.

To overcome sensorineural deafness, cochlear implant systems or cochlear prostheses have been developed that can bypass the hair cells located in the cochlea by presenting electrical stimulation directly to the auditory nerve fibers. This leads to the perception of sound in the brain and provides at least partial restoration of hearing function. Most of these cochlear prosthesis systems treat sensorineural deficit by stimulating the ganglion cells in the cochlea directly using an implanted electrode or lead that has an electrode array. Thus, a cochlear prosthesis operates by directly stimulating the auditory nerve cells, bypassing the defective cochlear hair cells that normally transduce acoustic energy into electrical activity to the connected auditory nerve cells.

Prior to stimulating the nerve cells, the electronic circuitry and the electrode array of the cochlear prosthesis separate acoustic signals into a number of parallel channels of information, each representing a narrow band of frequencies within the perceived audio spectrum. Ideally, each channel of information should be conveyed selectively to a subset of auditory nerve cells that normally transmit information about that frequency band to the brain. Those nerve cells are arranged in an orderly tonotopic sequence, from the highest frequencies at the basal end of the cochlear spiral to progressively lower frequencies towards the apex.

A cochlear implant system typically comprises both an external unit that receives and processes ambient sound waves and a cochlear implant that receives data from the external unit and uses that data to directly stimulate the auditory nerve. A common configuration for a cochlear implant system thus involves internal components that are surgically implanted into the patient and external components that provide power and electrical signals representing environmental sound to the internal components. These external components typically include a Behind-the-Ear (BTE) processor worn on the ear or a body worn processor. These processors contain a microphone, batteries, and signal circuitry that processes the electrical signals generated by the microphone. The processors are connected to a headpiece by a cable. The headpiece receives the electrical signals through the cable and transmits them to the internal components.

In some cochlear implant systems, the cable or cables connecting the external components together can present some issues. For example, the cable may have to be routed through clothing or accommodated during hair styling. The cable may be snagged, pulled on, or tangled, causing the headpiece to fall off. Additionally, cables are considered unattractive by many patients and are susceptible to failure due to bending.

An inductive link is commonly used to transmit telemetry signals from the external unit to the implanted cochlear stimulator. To this end, the external unit often includes an inductive coil that produces a telemetry signal by generating an electro-magnetic field that is picked up by a receiver on the implanted cochlear stimulator. The inductive coil may be housed in an external headpiece that is positioned on a patient's head to transmit the telemetry signal through the patient's scalp to the implanted receiver. The external unit often includes a retention magnet for securing the headpiece to the patient's head so that the induction coil is properly positioned adjacent to the implanted receiver.

In a conventional cochlear implant system, electronic circuitry included within the external unit is not placed in relative close proximity to the induction coil and the retention magnet due to losses and interference caused by magnetic flux associated with the induction coil and the retention magnet. Hence, the electronic circuitry is typically housed within a behind-the-ear unit, for example, while the induction coil and the retention magnet are housed separately within a headpiece. Such a configuration is undesirable for many cochlear implant patients.

BRIEF DESCRIPTION OF THE DRAWINGS

The accompanying drawings illustrate various embodiments of the principles described herein and are a part of the specification. The illustrated embodiments are merely examples and do not limit the scope of the claims.

Throughout the drawings, identical reference numbers designate similar, but not necessarily identical, elements.

DETAILED DESCRIPTION

Figure 1:
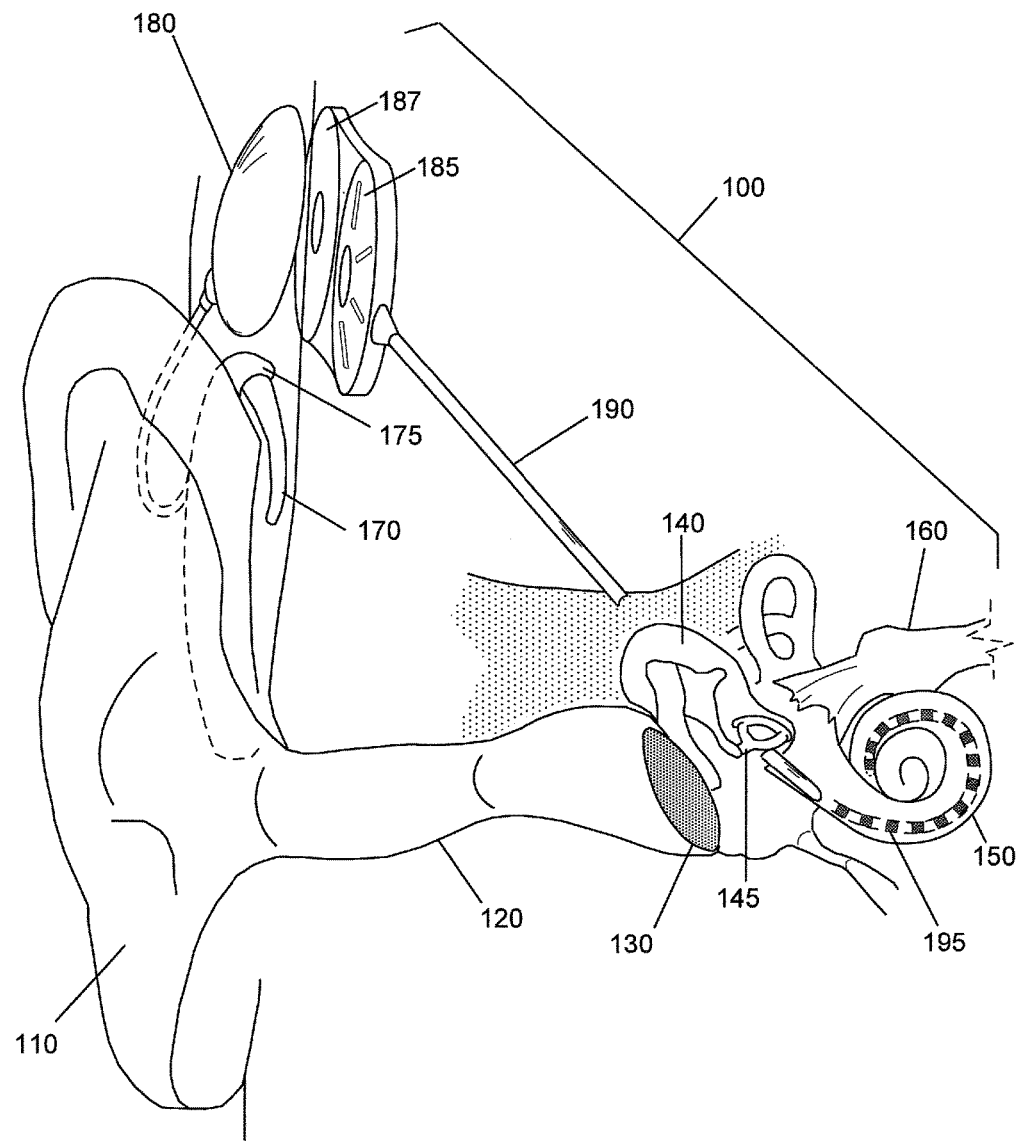
FIG. 1 is an illustrative diagram showing a cochlear implant system in use.

As mentioned above, individuals with hearing loss can potentially be helped by a number of different hearing assistance devices. These assistive devices are typically worn regularly and over a significant period of each day. Consequently, any such hearing assistance device should be robust and reliable. Additionally, the hearing assistance device should be visually unobtrusive and not unduly restrict the user's activities. As explained above, cochlear implant users typically must wear at least two separate external units, a processor and a headpiece, that are connected by a cable.

The processor may be a Behind-The-Ear (BTE) processor or a body worn processor. A BTE processor typically uses a hook which attaches over the top of the outer ear and holds the BTE processor in place behind the ear of the user. The BTE processor contains a microphone, battery, and electronics. A cable attaches the BTE processor to the headpiece and conveys data signals and power to the headpiece. The headpiece is typically held in place by magnetic forces generated by a surgically implanted magnet that is a part of the internal cochlear implant.

A body worn processor is typically worn by attaching the processor to an article of clothing worn by the user. For example, a body worn processor may be tucked into a pocket or attached to a lapel. The body worn processor does not have the severe size and weight constraints that are associated with a BTE processor. Consequently, the electronics and battery capacity of the body worn processor can be significantly greater than BTE processors. Like the BTE processor, a cable attaches the body worn processor to the headpiece.

As mentioned above, the cable or cables connecting the external components together can be difficult to manage. For example, when a child wears a cochlear implant, the parent may have to take additional care in dressing the child and restrict some activities the child would otherwise enjoy in order to reduce the chances of the cable being snagged, pulled on, tangled, or broken. Additionally, the processor and cable can be visually distracting and are considered unattractive by many patients. For some patients, the BTE unit can be uncomfortable, particularly those who are sensitive to heavy objects hanging from their ears.

Accordingly, the present specification addresses these issues by describing an integrated cochlear implant headpiece that combines the external components of the cochlear system into a single unit that is worn directly over the surgically implanted receiver. The integrated cochlear implant headpiece is a head mounted, external component unit which provides a stand-alone support for the functionalities of the implanted components. This eliminates the need for a separate body worn processor or BTE processor and the connecting cable. Consequently, the integrated cochlear implant headpiece reduces the difficulties commonly associated with wearing and using a cochlear implant. Specifically, because there is no separate processor unit or connecting cable, there is no need to route a cable through clothing or hair and no possibility of snagging or damaging the cable. Additionally, the integrated cochlear implant headpiece can be significantly less visually intrusive and more user friendly. The modular nature of the integrated cochlear implant headpiece may allow for other devices to communicate with and/or be attached to the integrated cochlear implant headpiece to provide additional functionality. However, the integrated headpiece is configured to provide the basic functionality for the operation of the cochlear implant as a stand alone unit.

In some embodiments, the integrated cochlear implant headpiece may have one or more accessories which attach to the integrated headpiece and provide additional functionality. As discussed in U.S. application Ser. No. 10/823,880 (now U.S. Pat. No. 7,599,508), of which the current application is a continuation-in-part, an assistive listening cap may magnetically attach to the top of the integrated cochlear implant. The assistive listening device may provide a variety of benefits to the patient. By way of example and not limitation, the assistive listening device may provide additional battery power; alternative antennas and circuitry for receiving audio signals via electromagnetic transmission; additional memory capacity; and/or additional signal processing capability.

Some exemplary cochlear implant systems include a circuit board having electronic circuitry configured to generate one or more signals configured to direct electrical stimulation of one or more stimulation sites within a patient, an induction coil configured to transmit a telemetry signal by generating a telemetry magnetic field, and a telemetry flux guide positioned between the induction coil and the circuit board. The telemetry flux guide is configured to direct magnetic flux of the telemetry magnetic field away from the circuit board.

Some exemplary cochlear implant systems include a circuit board having electronic circuitry configured to generate one or more signals configured to direct electrical stimulation of one or more stimulation sites within a patient, a retention magnet configured to produce a retention magnetic field for securing one or more components of the cochlear implant system to a head of said patient, and a retention flux guide positioned between the retention magnet and the circuit board. The retention flux guide is configured to direct magnetic flux of the retention magnetic field away from the circuit board.

Some exemplary external headpieces for use in cochlear implant systems include a circuit board having electronic circuitry configured to generate one or more signals configured to direct electrical stimulation of one or more stimulation sites within a patient. The external headpieces further include an induction coil configured to transmit a telemetry signal by generating a telemetry magnetic field and a telemetry flux guide positioned between the induction coil and the circuit board. The telemetry flux guide is configured to direct magnetic flux of the telemetry magnetic field away from the circuit board.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "an embodiment," "an example," or similar language means that a particular feature, structure, or characteristic described in connection with the embodiment or example is included in at least that one embodiment, but not necessarily in other embodiments. The various instances of the phrase "in one embodiment" or similar phrases in various places in the specification are not necessarily all referring to the same embodiment.

Throughout the specification, a cochlear implant system which includes a Behind-The-Ear (BTE) processor and headpiece is used as an example of a typical cochlear implant system. As used in the specification and appended claims the term "headpiece" refers to an external component that is located on the head in proximity to an internal receiver, as opposed to a BTE processor or body worn processor.

FIG. 1 is a diagram showing one illustrative embodiment of a cochlear implant 100 which is surgically placed within the patient's auditory system. Ordinarily, sound enters the outer ear 110 and is directed into the auditory canal 120 where the sound wave vibrates the tympanic membrane 130. The motion of the tympanic membrane is amplified and transmitted through the ossicular chain 140 which consists of three bones in the middle ear. The third bone of the ossicular chain, the stirrup 145, contacts the outer surface of the cochlea 150 and causes movement of the fluid within the cochlea 150. Cochlear hair cells respond to the fluid-borne vibration in the cochlea 150 and trigger neural electrical signals that are conducted from the cochlea 150 to the auditory cortex by the auditory nerve 160.

As indicated above, the cochlear implant 100 is a surgically implanted electronic device that provides a sense of sound to a person who is profoundly deaf or severely hard of hearing. In many cases, deafness is caused by the absence or destruction of the hair cells in the cochlea, i.e., sensorineural hearing loss. In the absence of properly functioning hair cells, there is no way auditory nerve impulses can be directly generated from ambient sound. Thus, conventional hearing aids, which amplify external sound waves, provide little benefit to persons suffering from significant sensorineural hearing loss.

Unlike hearing aids, the cochlear implant 100 does not amplify sound, but works by directly stimulating any functioning auditory nerve cells inside the cochlea 150 with electrical impulses. Cochlear prosthesis typically involves the implantation of electrodes into the cochlea. The cochlear implant operates by direct electrical stimulation of the auditory nerve cells, bypassing the defective cochlear hair cells that normally traduce acoustic energy into electrical energy.

External components of the cochlear implant system include a BTE unit 175 which contains the speech processor and has a microphone 170, a cable 177, and a transmitter 180. The microphone 170 picks up sound from the environment and converts it into electrical impulses. The speech processor within the BTE unit 175 selectively filters and manipulates the electrical impulses and sends the processed electrical signals through a cable 177 to the transmitter 180. The transmitter 180 receives the processed electrical signals from the processor and transmits them to the antenna 187 by electromagnetic induction and/or radio frequencies. In some cochlear implant systems, the transmitter 180 is held in place by magnetic attraction with the underlying antenna 187.

The internal components of the cochlear implant include an antenna 187, an internal processor 185, cochlear lead 190, and electrodes 195. The antenna 187 and internal processor 185 are secured beneath the user's skin, typically above and behind the external ear 110. As discussed above, the antenna 187 receives electromagnetic signals and power from the transmitter 180. These signals and power are transmitted using a wired connection to the internal processor 185. The internal processor 185 operates on the received signals and generates modified signals which are sent through the cochlear lead 190 to the electrodes 195. The electrodes 195 are wound through the cochlea 150 and provide direct electrical stimulation to the auditory nerve inside the cochlea 150.

The cochlear implant stimulates different portions of the cochlea 150 according to the frequencies detected by the microphone 170, just as a normal functioning ear would experience stimulation at different portions of the cochlea depending on the frequency of sound vibrating the liquid within the cochlea 150. This allows the brain to interpret the frequency of the sound as if the hair cells of the basilar membrane were functioning properly.

Figure 2:
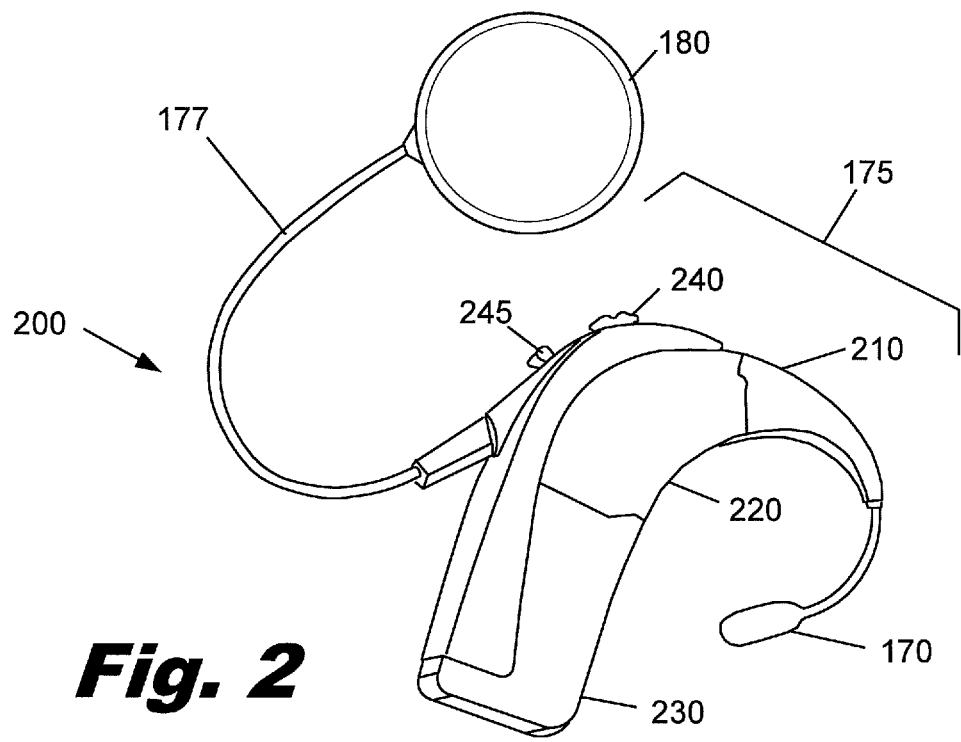
FIG. 2 is a diagram showing external components of an illustrative cochlear implant system.

FIG. 2 is an illustrative diagram showing a more detailed view of the external components 200 of one embodiment of a cochlear implant system. External components 200 of the cochlear implant system include a BTE unit 175 which comprises a microphone 170, an ear hook 210, a speech processor 220, and a battery 230, which may be rechargeable. The microphone 170 picks up sound from the environment and converts it into electrical impulses. The speech processor 220 selectively filters and manipulates the electrical impulses and sends the processed electrical signals through a cable 177 to the transmitter 180. A number of controls 240, 245 adjust the operation of the processor 220. These controls may include a volume switch 240 and program selection switch 245. The transmitter 180 receives the processed electrical signals from the processor 220 and transmits these electrical signals and power from the battery 230 to the internal components of the cochlear implant by electromagnetic induction, radio frequencies, optical communication, or any other wireless communication technology.

Figure 3:
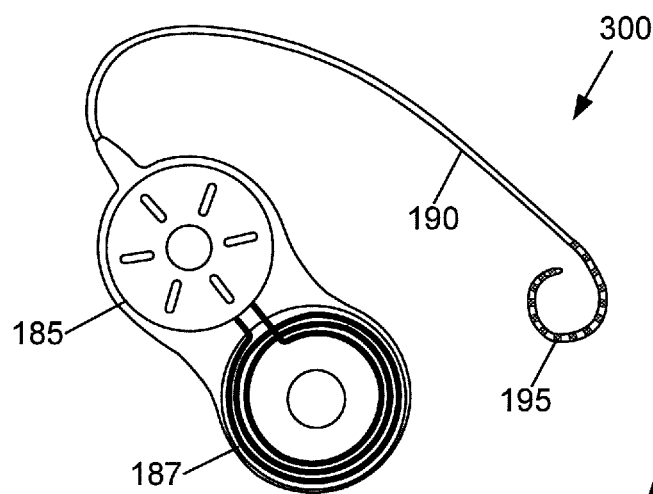
FIG. 3 is a diagram showing the internal components of an illustrative cochlear implant system.

FIG. 3 is an illustrative diagram showing the internal components 300 of one embodiment of a cochlear implant. These internal components 300 include an antenna 187, an internal processor 185, a cochlear lead 190, and electrodes 195. The internal components 300 of the cochlear implant are surgically implanted such that the electrodes 195 are internal to the cochlea, as shown in FIG. 1. The antenna 187 and the internal processor 185 are secured beneath the user's skin, typically above and behind the external ear, with the cochlear lead 190 connecting the internal processor 185 to the electrodes 195. As discussed above, the antenna 187 receives signals from the transmitter 180. These signals are then passed to the internal processor 185 which may perform various operations in the signals to produce modified signals which are particularly configured to be sent through the cochlear lead 190 to the electrodes 195. The electrodes 195 are wound through the cochlea and provide direct electrical stimulation to the auditory nerves inside the cochlea. This provides the user with sensory input that is a representation of external sound waves which were sensed by the microphone 170.

Figure 4:
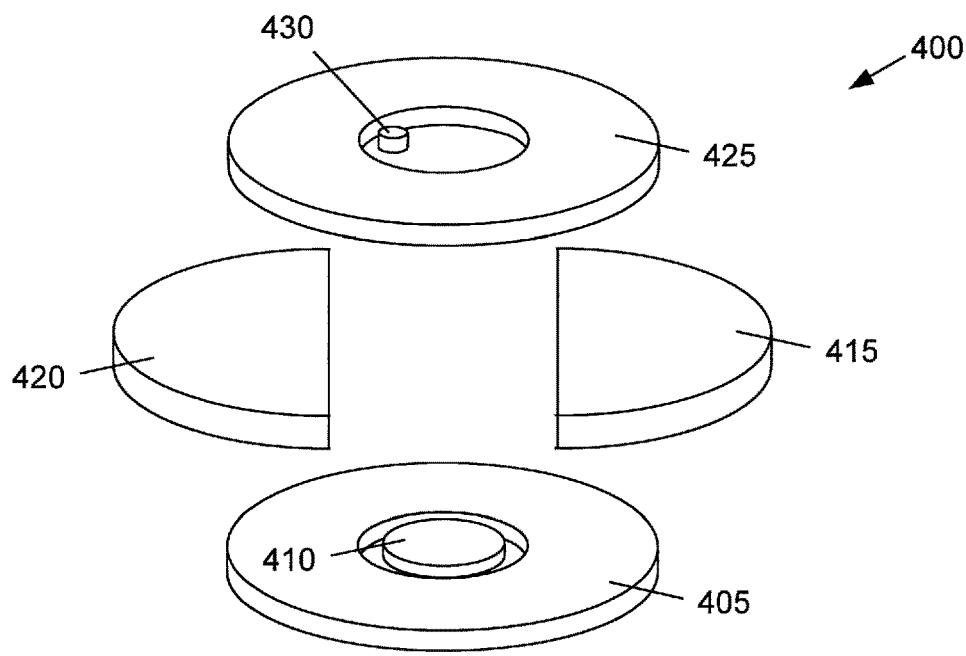
FIG. 4 is a diagram of various illustrative components which may make up an integrated headpiece, according to one embodiment of principles described herein.

FIG. 4 is an exploded view of components which may be included in an integrated headpiece 400. The integrated headpiece 400 may include a transmitter antenna 405, a magnet 410, a battery 415, electronics for audio signal processing 420, and a microphone 430. Headpiece 400 may also optionally include a receiver 425 for receiving signals from an external source.

As discussed above, the transmitter antenna 405 transmits signals to the implanted antenna 187 (FIG. 3). According to one embodiment, the transmitter antenna 405 also inductively transmits power to the internal components. The magnet 410 in the center of the transmitter antenna 405 is attracted to an implanted magnetic component that is in the center of the implanted antenna 187 (FIG. 3). The attraction between the magnet 410 and the implanted magnetic component holds the integrated headpiece 400 over the antenna 187 (FIG. 3). The transmitter antenna 405 may also be used to receive power to charge the battery 415 when the integrated headpiece 400 is not in use. For example, the transmitter antenna 405 could be used to inductively charge the battery by placing in the transmitter antenna in proximity to a charging coil through which an alternating current is passed. The transmitter coil acts as a transformer coil and receives a portion of the energy. This energy can then be used to charge the battery within the integrated headpiece. One advantage of using inductive coupling to charge batteries is that the headpiece can be more easily sealed because there is no need for exposed conductors or connectors.

The magnet 410 may be made from any of a number of magnetic materials including, but not limited to, neodymium-iron-boron, samarium-cobalt, ticonal, alnico, ceramic, magnetic powder in a resin matrix, or other suitable material. According to one embodiment, materials which exhibit a higher magnetic strength per unit volume may be used to minimize the size of the magnet and integrated headpiece 400.

The battery 415 supplies electrical energy that is required for the function of the cochlear implant. Important considerations for a battery included in the integrated headpiece may include the energy density, total capacity of the battery, voltage, robustness, the ability to hold a charge over a long period of time, and the ability to be repeatedly charged and discharged.

By way of example and not limitation, the battery may a lithium ion battery, a polymer lithium battery, a zinc air battery or other suitable battery. Polymer lithium batteries operate using the same chemistry as conventional lithium ion batteries but contain the lithium-salt electrolyte within a solid polymer composite rather than a rigid metal case. Consequently, polymer lithium batteries can be lighter, more energy dense, and less vulnerable to physical damage. Further, polymer lithium batteries can be specifically shaped to fit the device it will power. Zinc air batteries operate by the oxidation of zinc with atmospheric oxygen. Zinc air batteries have high energy densities and are relatively inexpensive to produce. However, to operate, zinc air batteries must have direct exposure to the atmosphere, which creates challenges in using these batteries in sealed systems.

The electronics 420 may include components and functionality such as power conditioning electronics, signal processors, filters, amplifiers, receivers, switches, memory, and other electronics. The principal function of the electronics 420 is to receive an audio signal from the microphone 430 and process that signal into a signal that can be transmitted to the implanted unit to drive stimulation of the cochlea.

A number of additional components may be included in the integrated headpiece. For example, various visual indicators, such as one or more light emitting diodes, could also be included. These visual indicators could be configured to communicate information regarding the function of both internal and external components of the cochlear implant system, such as battery status, the selected program, sensitivity or volume information, and communication status between the headpiece and implanted receiver.

The integrated headpiece may optionally include a receiver 425. The receiver 425 may be any one of a variety of radio frequency (RF), WiFi, IEEE 802.11, Bluetooth®, or other receivers. These receivers can directly link the cochlear implant system to sound sources, reducing undesirable interference by other noise sources. The sound sources may include a wireless microphone, a remote control device, a cell phone, a computer, a music player, a personal digital assistant, or other device. For example, in an educational setting, teacher may wear a wireless microphone which transmits the teacher's voice over a radio frequency directly to a receiver contained within the integrated headpiece. Similarly, a Bluetooth® receiver could be connected to a stereo, cell phone, or other audio source.

A microphone 430 is also included within the integrated headpiece. The microphone 430 may reside directly on the electronics component or may be a separate component that sends electrical signals through a wired connection to the electronics. A variety of microphone types and configurations may be used. By way of example and not limitation, the microphone may use electromagnetic, capacitance change, MicroElectroMechanical Systems (MEMS) or piezoelectric mechanisms to produce an electrical signal from mechanical vibrations induced by sound. The microphone may also have one of many directional sensitivity profiles. For example, the microphone may have an omnidirectional, hemispherical, subcardioid, cardioid, or highly directional sensitivity profile.

Figure 5:
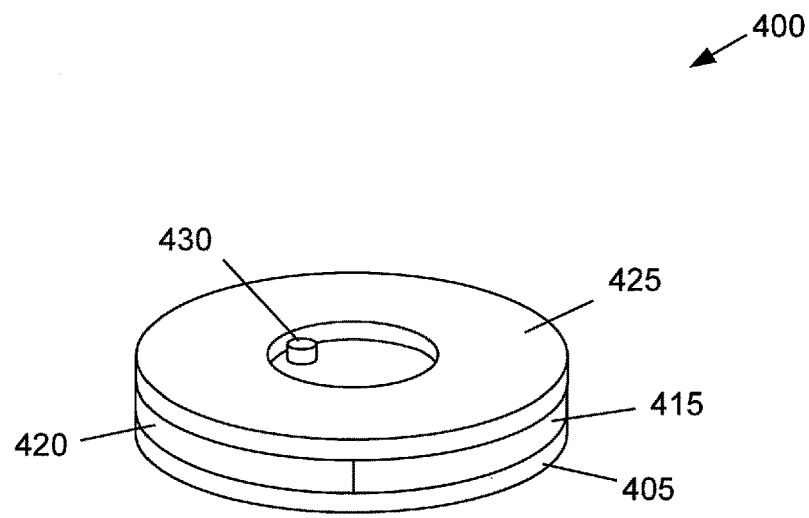
FIG. 5 is a perspective view of an illustrative integrated headpiece, according to one embodiment of principles described herein.

FIG. 5 is a diagram showing the components of the illustrative integrated headpiece 400 in an assembled configuration. As mentioned above, the integrated headpiece 400 consolidates all of the external components of the cochlear implant system in one compact unit. This eliminates cables connecting the traditional components together and the associated problems of routing the cables through clothing or the cable being snagged, pulled on, or tangled, causing the headpiece to fall off. Additionally, the integrated headpiece 400 may be more discrete than systems with multiple components. For example, the integrated headpiece 400 may be completely covered by the user's hair or hat. Further, the integrated headpiece 400 may be more robust than multiple component configurations. The integrated headpiece 400 may be much easier to seal because there is no need for external connection or cables.

Figure 6:
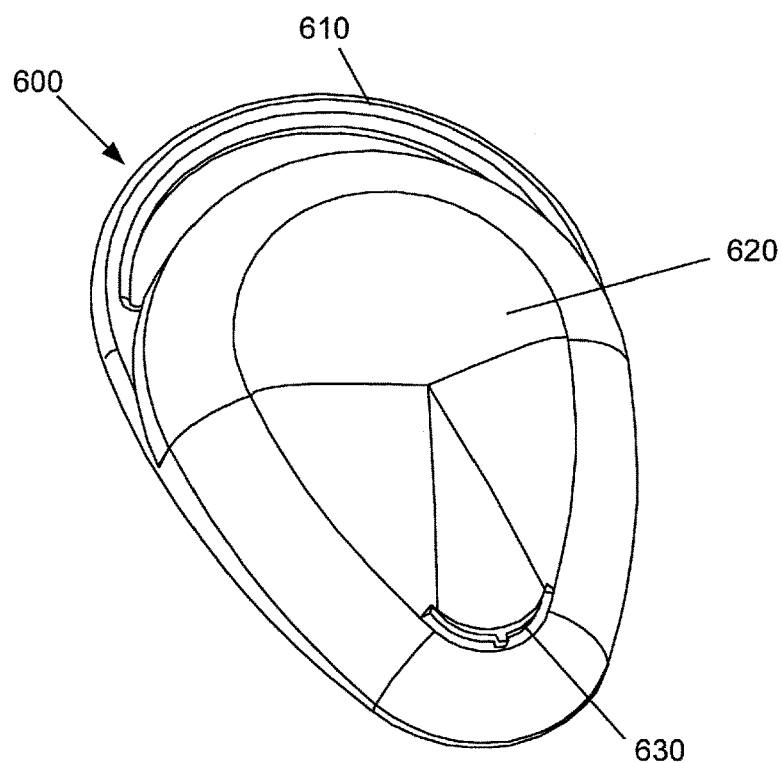
FIG. 6 is a perspective view of an illustrative integrated headpiece, according to one embodiment of principles described herein.

The components illustrated in FIGS. 4 and 5 can be configured in a number of different shapes and contained with a variety of housings. FIG. 6 shows one illustrative configuration of an integrated headpiece 600. In this illustrative embodiment, a body portion 620 contains the battery, electronics, microphone, and magnet.

A portion of the transmitter antenna 610 extends beyond the body portion 620, forming an open loop. This transmitter antenna configuration may have a number of advantages that extend beyond the visual appearance of the headpiece 600. For example, the transmitter antenna 610 may additionally serve as an inductive pick up which receives electrical energy from an exterior coil to charge the internal battery.

The exposed portion of the transmitter antenna 610 may also allow for more efficient transfer of the electrical power from the exterior coil because the exterior coil could substantially surround the transmitter antenna. In one charging configuration, the exposed portion of the transmitter antenna 610 may be inserted into a corresponding slot in a charging platform. One or more charging coils could be placed on either side of the slot. The transmitter antenna 610 would then be in very close proximity to the charging coils. Additionally, the exposed portion transmitter antenna 610 could assist in the proper positioning and retention of the integrated headpiece 600 within the charging platform.

The integrated headpiece may also have a number of other features. As mentioned above, visual indicators could be incorporated into the external shell of the integrated headpiece to allow a caretaker to visually ascertain the state and functionality of the integrated headpiece. By way of example and not limitation, the indicating features may include light emitting diodes which indicate the battery condition. For example, as the battery discharges, a light emitting diode is illuminated to indicate the need to recharge or replace the battery. This could be advantageous for a parent or teacher who can visually determine the battery level.

Similarly, the integrated headpiece may have one or more visual elements which indicate the state of the cochlear implant. For example, a light emitting diode could have a first color and illumination pattern which indicates that cochlear implant is operational. The light emitting diode could have a different color and/or illumination pattern for various malfunctions such as a malfunction of the integrated headpiece, lack of communication between the integrated headpiece and implanted receiver, or a receiver malfunction.

In the illustrative embodiment shown in FIG. 6, a switch 630 is included to allow the user to adjust the amplification of the device or to switch between a number of predetermined programs. For example, a first program may be specially adapted for personal conversations with minimal background noise, while a second program may be optimized for environments with much higher levels of background noise, such as a restaurant or crowded convention venue. A third program setting may activate a Radio Frequency (RF) receiver that is linked to a microphone worn by a teacher, lecturer, or conversationalist. By including external switches, the user can adjust the integrated headpiece in real time to suit a particular sound environment.

Figure 7:
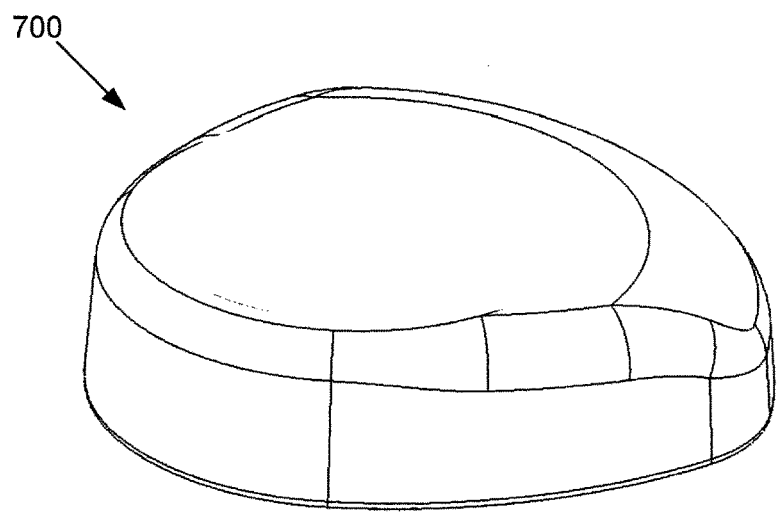
FIG. 7 is a perspective view of an illustrative integrated headpiece, according to one embodiment of principles described herein.

FIG. 7 is a perspective view of an illustrative integrated headpiece 700. In this illustrative embodiment, the exterior profile of the headpiece 700 is simplified, which may result in a more robust and inexpensive device. This common rigid housing contains the microphone, signal processing electronics, transmitter and power supply. The rigid housing maintains its shape during normal handling and provides protection for the internal components against external contaminants and impact. Additionally, external switches and visual indicators may be omitted from the headpiece. By eliminating these external features, the headpiece may be more easily constructed to be waterproof, allowing the user to walk in the rain, swim, or participate in water sports without removing the headpiece. This will allow the user to continue to receive auditory signals, thereby enhancing the user's enjoyment of the activity, ability to interact with others, and increasing the user's safety.

According to one embodiment, the headpiece may be linked via a receiver in the headpiece to an external control unit. For example, a number of controls could be incorporated into a key fob. By pressing buttons on the key fob, wireless signals could be sent to adjust the operational parameters of the integrated headpiece.

Figure 8:
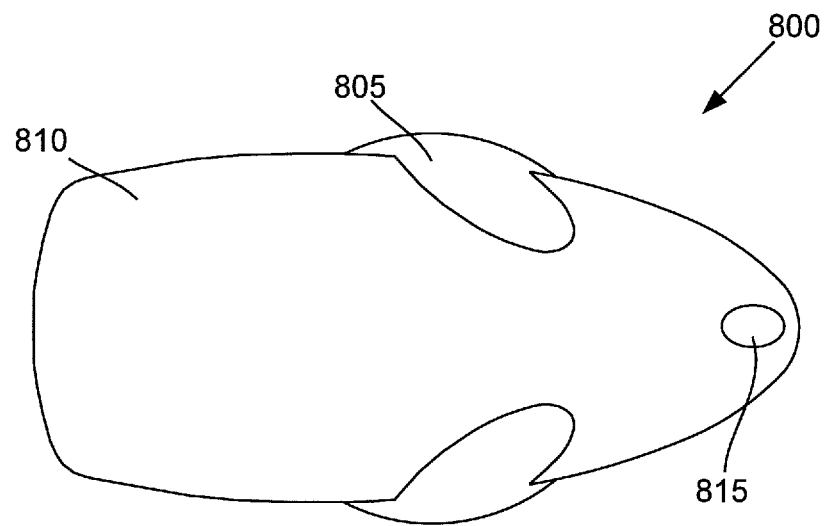
FIG. 8 is a top view of an illustrative integrated headpiece, according to one embodiment of principles described herein.

FIG. 8 is a top view of an illustrative integrated headpiece 800 with an alternative geometry. In this illustrative embodiment, the transmitter antenna may be contained within a center portion 805 of the integrated headpiece 800. Other components may be contained within the body portion 810. According to one illustrative embodiment, the integrated headpiece 800 may additionally include a directional microphone 815. Typically, omnidirectional or hemispherical microphones are used in cochlear devices to better replicate the sensitivity of the human ear. However, in some circumstance it may be beneficial to more selectively sense external sounds, thereby reducing background noise. The directional microphone 815 can be used by the patient to selectively amplify selected sound sources. According to one embodiment, the directional microphone 815 may be pointing in the same direction the patient is looking. For example, a patient may simply turn his head toward one who is speaking to point the directional microphone 815 in the speaker's direction to preferentially sense his voice.

The lower cost and ease of wearing the integrated headpiece can lead to a number of benefits. For example, the patient may have two or more integrated headpieces. While one integrated headpiece is being worn by the user, the other integrated headpiece can be recharging its battery.

Additionally or alternatively, the functionality provided by a second integrated headpiece may be different. The user can then select the integrated headpiece that is most appropriate for the situation. For example, during a social event, the user may select an integrated headpiece that is less obtrusive or complements other clothing accessories. During the course of a normal day, the user may select an integrated headpiece with a longer lifetime or with a needed receiver. For example, if the user attends school, the user may need a battery that can supply power throughout the school day and a receiver that can receive amplified/filtered signals from a wireless microphone worn by the teacher. If the user is participating in water activities, a sealed headpiece could be selected.

Figure 9:
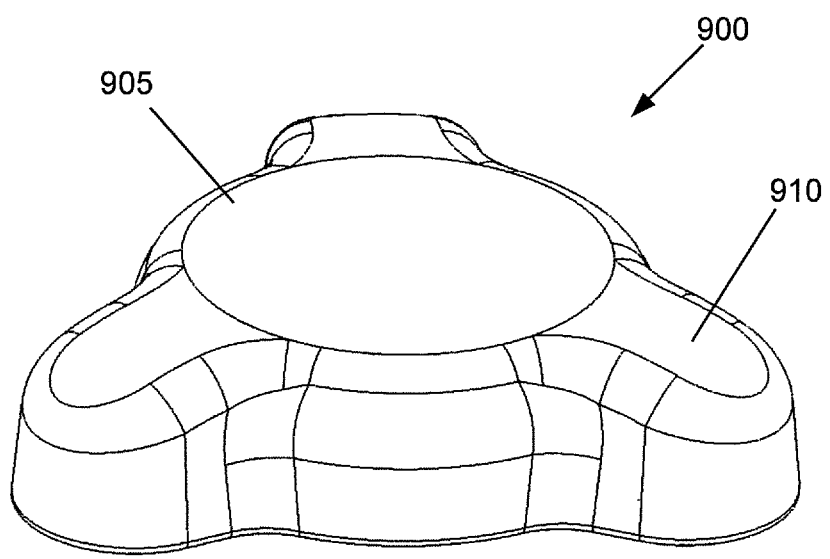
FIG. 9 is a perspective view of an illustrative integrated headpiece, according to one embodiment of principles described herein.

FIG. 9 is a perspective view of an illustrative integrated headpiece 900 with an alternative geometry. According to one embodiment, the integrated headpiece 900 has a number of lobes 910 which surround a central body portion 905. These lobes 910 may serve a number purposes including increasing the stability of the headpiece, creating a visually interesting profile, increasing the internal volume of the integrated headpiece 900, providing a shape that is adapted to a particular transmitter or receiver, or covering a lithium polymer battery which is particularly shaped to be received by the lobes 910.

Figure 10:
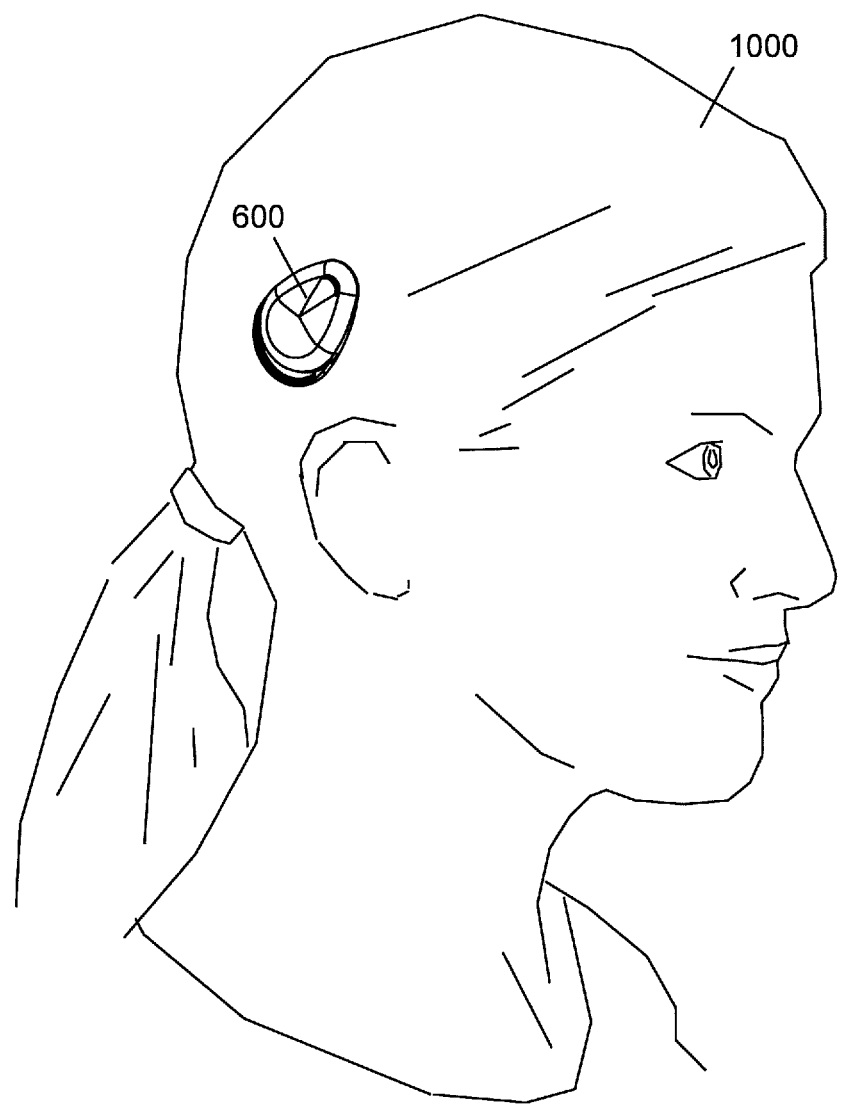
FIG. 10 is a diagram showing an illustrative integrated headpiece being worn by a user, according to one embodiment of principles described herein.

FIG. 10 shows an illustrative integrated headpiece 600 being worn by a user 1000. As discussed above, an integrated headpiece is worn over the antenna implantation site. The antenna is typically implanted above and behind the external ear as shown in FIG. 10. However, the antenna may be implanted in a variety of other locations.

If desired, the user 1000 can conceal the integrated headpiece 600 by altering her hair style or wearing a head covering such as a hat, hood, or scarf. If the user has access to a variety of integrated headpieces, the user 1000 can select the integrated headpiece that is most suited for a given activity or day. The user may carry one or more backup headpieces in a pocket, purse, or backpack. If circumstances during the day make it desirable to replace the current integrated headpiece with an alternative headpiece, the user 1000 can simply reach up, grasp the integrated headpiece 600 and remove it. A second integrated headpiece is then retrieved, oriented with the magnet side toward the head, and brought to the approximate location of the implanted antenna. As the second integrated headpiece nears the antenna location, the magnetic attraction between the two magnetic components moves the integrated headpiece into the correct location and holds the integrated headpiece in place.

In sum, an integrated headpiece combines the external components of the cochlear implant system into a single unit that is worn directly over the surgically implanted receiver. This eliminates the need for a separate body worn processor or BTE processor and the connecting cable. Consequently, the integrated headpiece reduces the complexity of wearing and using a cochlear implant. The integrated headpiece eliminates the need to route a cable through clothing or hair and the possibility of snagging a cable. Additionally, the integrated headpiece can be more robust, modular, and significantly less visually intrusive than processors of conventional cochlear implant systems.

The telemetry flux guide and techniques for using the same to direct magnetic flux away from the circuitry in a cochlear implant that are described below with reference to FIGS. 11A-16 may be used in the devices and methods described above with reference to FIGS. 1-10 to control magnetic flux within a cochlear implant device or system.

Cochlear implant systems including an external headpiece that houses a circuit board having electronic circuitry configured to generate one or more signals configured to control an operation of an implantable cochlear stimulator are described herein. The external headpiece further includes an induction coil configured to transmit a telemetry signal to the implantable cochlear stimulator by generating a telemetry magnetic field. The external headpiece may additionally include a telemetry flux guide positioned between the induction coil and the circuit board. The telemetry flux guide may be configured to direct magnetic flux of the telemetry magnetic field away from the circuit board.

In some examples, the external headpiece further includes a retention magnet configured to produce a retention magnetic field for securing the headpiece to a head of the patient. In this case, the external headpiece may also include a retention flux guide positioned between the retention magnet and the circuit board. The retention flux guide may be configured to direct magnetic flux of the retention magnetic field away from the circuit board.

Figure 11A:
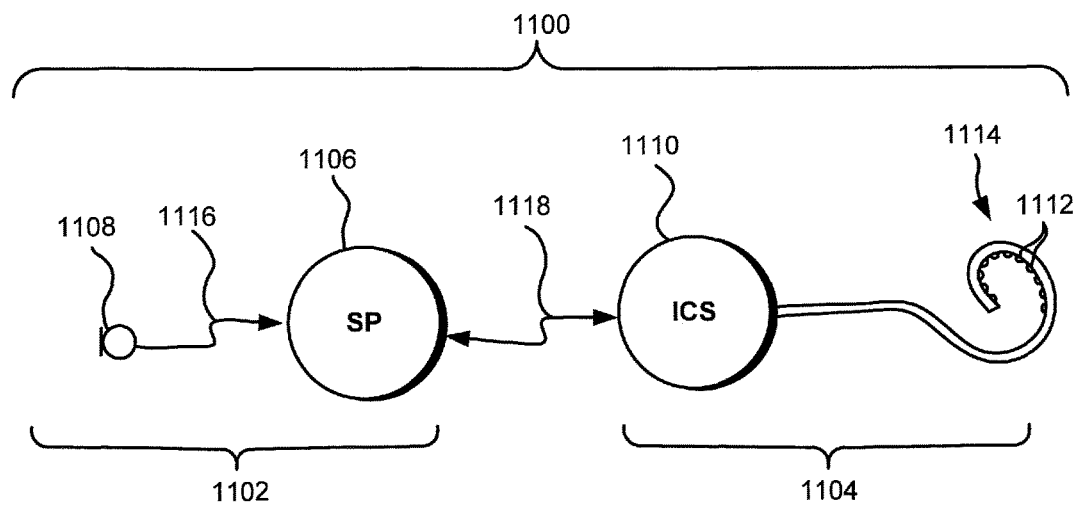
FIG. 11A illustrates an exemplary cochlear implant system according to principles described herein.

FIG. 11A illustrates an exemplary cochlear implant system 1100. Exemplary cochlear implant systems suitable for use as described herein include, but are not limited to, those disclosed in U.S. Pat. Nos. 6,219,580; 6,272,382; and 6,308,101, all of which are incorporated herein by reference in their respective entireties. The cochlear implant system 1100 of FIG. 11A includes a sound processor portion 1102 and a cochlear stimulation portion 1104. The sound processor portion 1102 may include a sound processor 1106, a microphone 1108, and/or additional circuitry as best serves a particular application. The cochlear stimulation portion 1104 may include an implantable cochlear stimulator 1110, a number of electrodes 1112 disposed on an electrode lead 1114, and/or additional circuitry as best serves a particular application. The components within the sound processor portion 1102 and the cochlear stimulation portion 1104 will be described in more detail below.

The microphone 1108 of FIG. 11A is configured to sense audio signals and convert the sensed signals to corresponding electrical signals. In some examples, the audio signal may include speech. The audio signal may additionally or alternatively include music, noise, and/or other sounds. The electrical signals are sent from the microphone 1108 to the sound processor 1106 via a communication link 1116. Alternatively, the microphone 1108 may be connected directly to, or integrated with, the sound processor 1106. The sound processor 1106 processes these converted audio signals in accordance with a selected sound processing strategy to generate appropriate stimulation parameters for controlling the implantable cochlear stimulator 1110. These stimulation parameters may specify or define the polarity, magnitude, location (i.e., which electrode pair or electrode group receive the electrical stimulation), stimulation rate, timing (i.e., when the electrical stimulation is to be applied to a particular electrode pair), spectral tilt, and/or any other characteristic of the electrical stimulation that is generated by the implantable cochlear stimulator 1110.

The electrode lead 1114 shown in FIG. 11A is configured to be inserted within a duct of a cochlea. As shown in FIG. 11A, the electrode lead 1114 includes a multiplicity of electrodes 1112, e.g., sixteen electrodes, spaced along its length. It will be understood, however, that any number of electrodes 1112 may be disposed on the electrode lead 1114. The electrode lead 1114 may be substantially as shown and described in U.S. Pat. No. 4,819,647 or U.S. Pat. No. 6,218,753, each of which is incorporated herein by reference in its respective entirety. As will be described in more detail below, electronic circuitry within the implantable cochlear stimulator 1110 is configured to generate and apply electrical stimulation to one or more stimulation sites within the cochlea via selected stimulation channels (i.e., pairs or groups of the individual electrodes 1112) in accordance with a specified stimulation strategy defined by the sound processor 1106.

In some examples, the sound processor 1106 and the microphone 1108 comprise an external portion of the cochlear implant system 1100, and the implantable cochlear stimulator 1110 and the electrode lead 1114 comprise an implantable portion of the system 1100 that is implanted within a patient's body. In alternative embodiments, one or more portions of the sound processor 1106 are included within the implantable portion of the cochlear implant system 1100.

The implantable cochlear stimulator 1110 and the sound processor 1106 may be communicatively coupled via a suitable data or communication link 1118, such as a telemetry communication link, as will be described in more detail below. It will be understood that the data communication link 1118 may include a bi-directional communication link and/or one or more dedicated uni-directional communication links. In some examples, the external and implantable portions of the cochlear implant system 1100 may each include one or more inductive coils configured to transmit and receive power and/or control signals via the communication link 1118. The control signals may include, for example, the magnitude and polarity of electrical stimulation representing a sensed audio signal. The external coil may also transmit power from the external portion to the implantable portion of the cochlear implant system 1100. Power transmitted to the implantable portion may be used to operate the implantable portion.

Figure 11B:
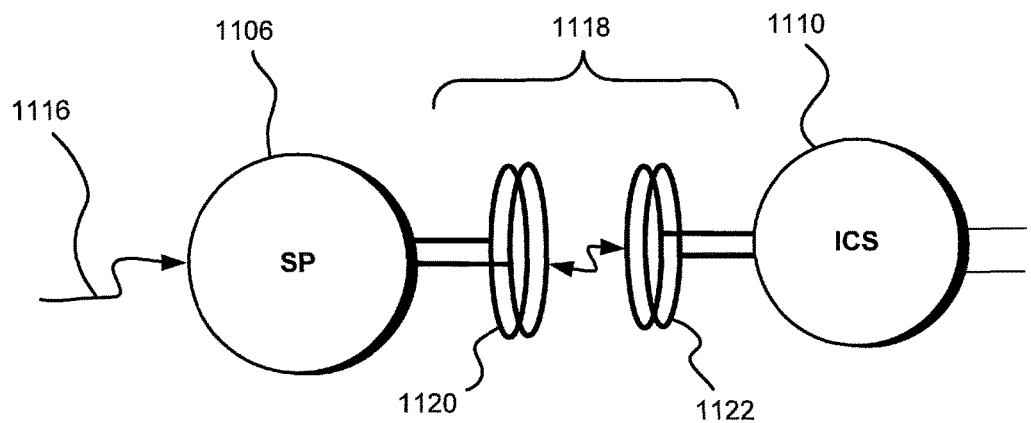
FIG. 11B illustrates a portion of an exemplary cochlear implant system according to principles described herein.

FIG. 11B illustrates a portion of an exemplary cochlear implant system showing a communication link 1118 comprising a telemetry communication link that may be used in accordance with the present systems and methods. As illustrated in FIG. 11B, an external portion of the cochlear implant system 1100 may include an external induction coil 1120 and an implantable portion of the cochlear implant system 1100 may include an implantable induction coil 1122. The external induction coil 1120 may be communicatively coupled to the sound processor 1106 and the implantable induction coil 1122 may be communicatively coupled to the implantable cochlear stimulator 1110.

The external induction coil 1120 and the implantable induction coil 1122 may include any suitable type of coil capable of generating and/or receiving an electromagnetic field. For example, the external induction coil 1120 and the implantable induction coil 1122 may each include a metallic wire or tube wound in a coiled or otherwise looped configuration. An alternating current may be directed from the sound processor 1106 through the external induction coil 1120, thereby generating a magnetic field surrounding the external induction coil 1120. The external induction coil 1120 may be positioned near the implantable induction coil 1122 such that the implantable induction coil 1122 is positioned at least partially within the magnetic field generated by the external induction coil 1120. The magnetic field generated by the external induction coil 1120 may cause an electric current to be generated in the internal induction coil 1120. The electric current generated in the internal induction coil 1120 may be directed from the internal induction coil 1120 to the implantable cochlear stimulator 1110. Accordingly, an electric current generated by the sound processor 1106 may be transferred to the implantable cochlear stimulator 1110 through the communication link 1118 comprising the external induction coil 1120 and the implantable induction coil 1122.

The communication link 1118 may function as a telemetry link between the sound processor 1106 and the implantable cochlear stimulator 1110. For example, the external induction coil 1120 may transmit one or more telemetry signals to the implantable induction coil 1122 by generating a telemetry magnetic field as electric current is passed through the external induction coil 1120. The telemetry magnetic field generated by the external induction coil 1120 may produce an electric current in the implantable induction coil 1122, as described above. The current generated in the implantable induction coil 1122 by the telemetry magnetic field generated by the external induction coil 1120 may be used to transfer signals representative of data and/or other information to the implantable cochlear stimulator 1110 and/or may be used to transfer power to the implantable cochlear stimulator 1110.

In some examples, the communication link 1118 may be used to transmit telemetry signals from the implantable cochlear stimulator 1110 to the sound processor 1106. For example, data acquired by the electrodes 1112 and/or status indicators generated by the cochlear stimulator 1112 may be transmitted to sound processor 1106 via the communication link 1118. To this end, implantable induction coil 1122 may transmit telemetry signals to the external induction coil 1120 by generating a telemetry magnetic field. The implantable cochlear stimulator 1110 may cause a current to flow through the implantable induction coil 1122 to generate the telemetry magnetic field. The external induction coil 1120 may be positioned at least partially within the telemetry magnetic field generated by the implantable induction coil 1122. The magnetic field may cause an electric current to be generated in the external induction coil 1120. The current generated in the external induction coil 1120 may be used to transfer data and/or other signals to the sound processor 1106.

The communication link 1118 may include more than one external induction coil 1120 and/or more than one implantable induction coil 1122. For example, a first external induction coil and a first implantable induction coil may be used to transfer data and/or power from the sound processor 1106 to the implantable cochlear stimulator 1110. A second external induction coil and a second implantable induction coil may be used to transfer data from the implantable cochlear stimulator 1110 to the sound processor 1106.

Figure 12:
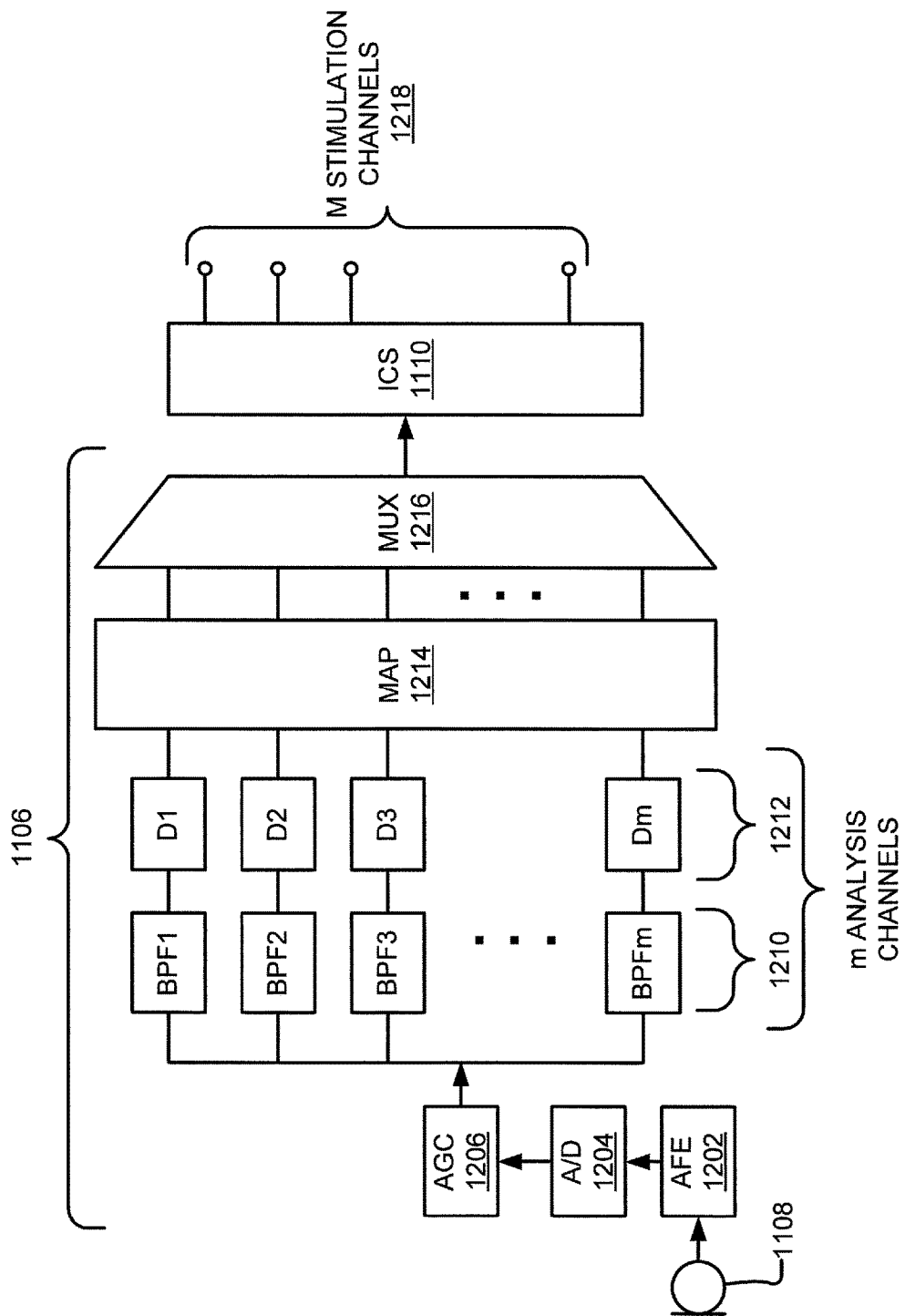
FIG. 12 is a functional block diagram of an exemplary sound processor and implantable cochlear stimulator according to principles described herein.

FIG. 12 is a functional block diagram of an exemplary sound processor 1106 and implantable cochlear stimulator 1110. The functions shown in FIG. 12 are merely representative of the many different functions that may be performed by the sound processor 1106 and/or the implantable cochlear stimulator 1110.

As shown in FIG. 12, the microphone 1108 senses an audio signal, such as speech or music, and converts the audio signal into one or more electrical signals. These signals are then amplified in audio front-end (AFE) circuitry 1202. The amplified audio signal is then converted to a digital signal by an analog-to-digital (ND) converter 1204. The resulting digital signal is then subjected to automatic gain control using a suitable automatic gain control (AGC) function 1206.

After appropriate automatic gain control, the digital signal is then processed in one of a number of digital signal processing or analysis channels 1208. For example, the sound processor 1106 may include, but is not limited to, sixteen analysis channels 1208. Each analysis channel 1208 may respond to a different frequency band of the sensed audio signal due to a series of band pass filters 1210.

As shown in FIG. 12, each of them analysis channels 1208 may also include an energy detection stage (D1-Dm) 1212. Each energy detection stage 1212 may include any combination of circuitry configured to detect the amount of energy contained within each of the m analysis channels 1208. For example, each energy detection stage 1212 may include a rectification circuit followed by an integrator circuit.

After energy detection, the signals within each of the m analysis channels 1208 are forwarded to a mapping stage 1214. The mapping stage 1214 is configured to map the signals in each of the m analysis channels 1208 to one or more of M stimulation channels 1218. In other words, the information contained in the m analysis channels 1208 is used to define the electrical stimulation pulses that are applied to the patient by the implantable cochlear stimulator 1110 via the M stimulation channels 1218. As mentioned previously, pairs or groups of individual electrodes 1112 may make up the M stimulation channels 1218.

In some examples, the mapped signals are serialized by a multiplexer 1216 and transmitted to the implantable cochlear stimulator 1110. The implantable cochlear stimulator 1110 may then apply electrical stimulation via one or more of the M stimulation channels 1218 to one or more stimulation sites within the duct of the patient's cochlea. As used herein, the term "stimulation site" will be used to refer to a target area or location to which the electrical stimulation is applied. For example, a stimulation site may refer to any location within a region of auditory nerve tissue (e.g., auditory nerve tissue 1306 shown in FIG. 13).

Figure 13:
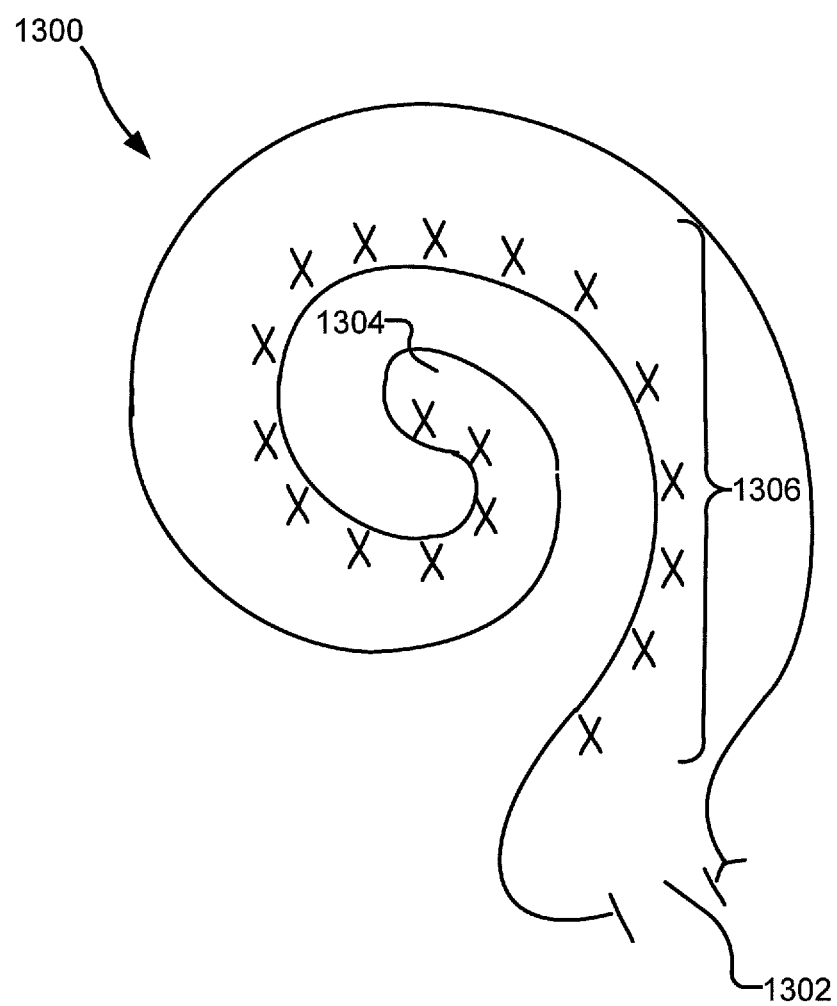
FIG. 13 illustrates a schematic structure of the human cochlea highlighting elements according to principles described herein.

FIG. 13 illustrates a schematic structure of the human cochlea 1300. As shown in FIG. 13, the cochlea 1300 is in the shape of a spiral beginning at a base 1302 and ending at an apex 1304. Within the cochlea 1300 resides auditory nerve tissue 1306, which is denoted by Xs in FIG. 13. The auditory nerve tissue 1306 is organized within the cochlea 1300 in a tonotopic manner. Low frequencies are encoded at the apex 1304 of the cochlea 1300 while high frequencies are encoded at the base 1302. Hence, each location along the length of the cochlea 1300 corresponds to a different perceived frequency. A cochlear prosthesis may therefore be implanted within a patient with sensorineural hearing loss and configured to apply electrical stimulation to different locations within the cochlea 1300 to provide the sensation of hearing. For example, electrode lead 1114 may be disposed within the cochlea 1300 such that electrodes 1112 contact auditory nerve tissue 1306 within the cochlea 1300. Electrical stimulation may be applied by the electrodes 1112 to the auditory nerve tissue 1306.

Figure 14:
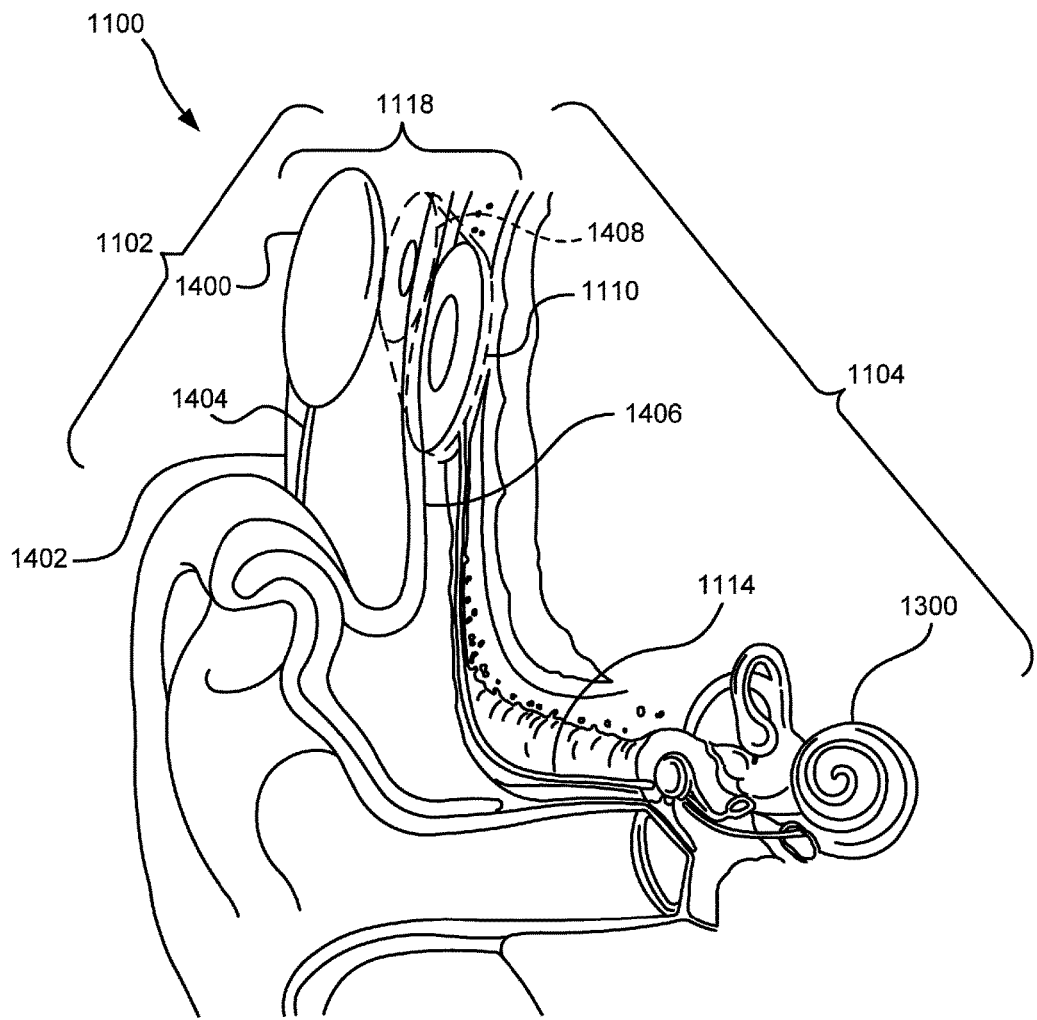
FIG. 14 illustrates an exemplary configuration of a cochlear implant system according to principles described herein.

FIG. 14 illustrates an exemplary configuration of cochlear implant system 1100 that may be used to apply electrical stimulation one or more stimulation sites within the cochlea 1300. As shown in FIG. 14, the external portion of the cochlear implant system 1100 may include an external headpiece 1400 configured to be worn on an exterior of a head 1402 of the patient. The external headpiece 1400 may include various components of the sound processor portion 1102, including the external induction coil 1122 (not shown), as will be described in greater detail below. The external headpiece 1400 may additionally include electronic circuitry, such as circuitry comprising at least a portion of the sound processor 1106. The external headpiece 1400 may be electrically connected, either directly or indirectly, to a microphone 1108 (not shown) positioned in or near the patient's ear via a communication line 1404. The headpiece 1400 may additionally include a retention magnet to position and maintain the headpiece 1400 in a proper orientation on the head 1402, as will be described in greater detail below.

As shown in FIG. 14, an implantable cochlear stimulator 1110 may be disposed underneath the skin 1406 of the patient. A lead 1114 with a plurality of electrodes 1112 disposed on a distal portion thereof may be coupled to the implantable cochlear stimulator 1110 and positioned such that the electrodes 1112 are disposed within the cochlea 1300.

In some examples, the implantable cochlear stimulator 1110 may include a receiver 1408 configured to facilitate communication with the external headpiece 1400. The receiver 1408 may include the implantable induction coil 1122 (not shown) described above.

The external induction coil 1120 in the external headpiece 1400 and the implantable induction coil 1122 in the receiver 1408 may form communication link 1118. As described above, data and/or power may be transmitted between the sound processor portion 1102 and the cochlear stimulation portion 1104 via the communication link 1118. For example, the external induction coil 1120 in the external headpiece 1400 may transmit a telemetry signal across the skin 1406 to the implantable induction coil 1122 in the receiver 1408. Additionally or alternatively, the implantable induction coil 1122 in the receiver 1408 may transmit a telemetry signal across the skin 1406 to the external induction coil 1120 in the external headpiece 1400.

Figure 15A:
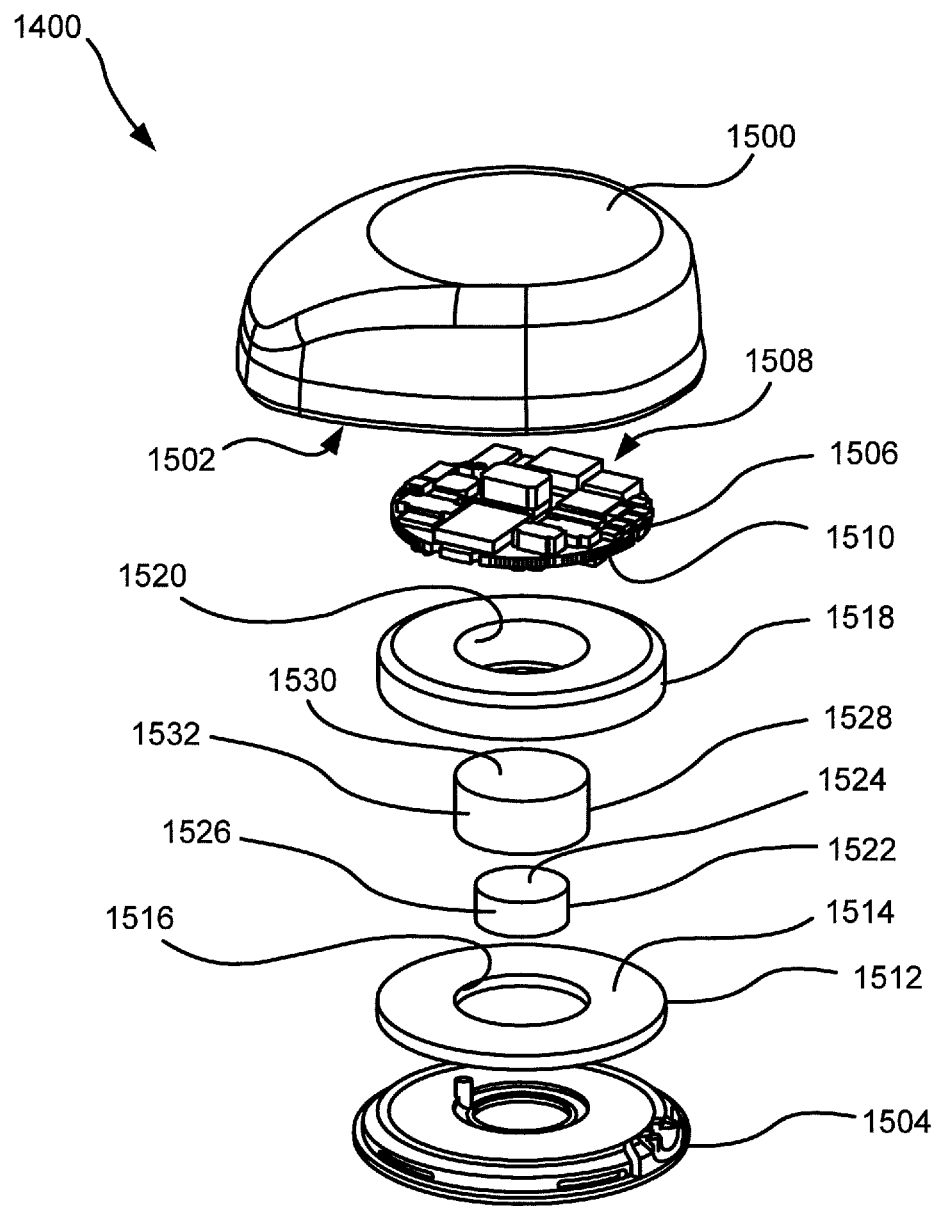
FIG. 15A is an exploded perspective view of an exemplary external headpiece according to principles described herein.
Figure 15B:
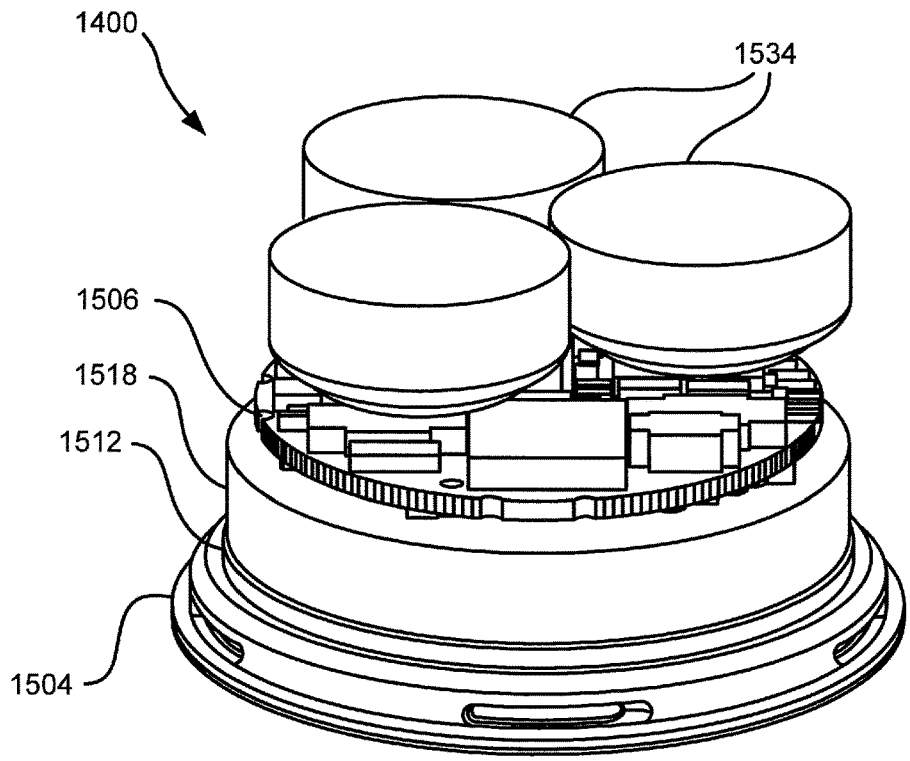
FIG. 15B is a perspective view of a portion of an exemplary external headpiece according to principles described herein.
Figure 15C:
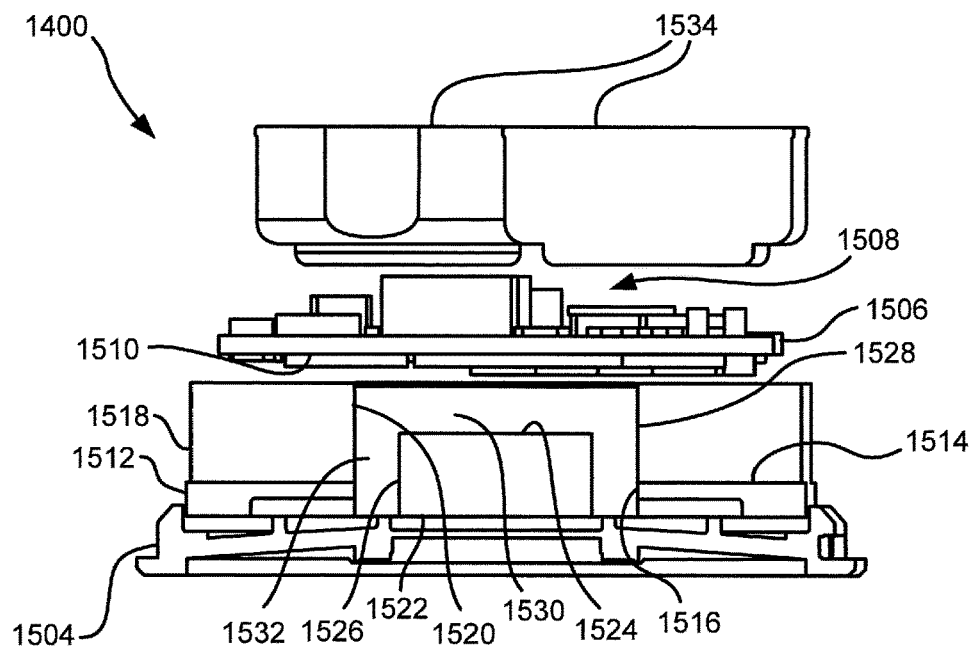
FIG. 15C is a cross-sectional side view of a portion of an exemplary external headpiece according to principles described herein.

FIGS. 15A-15C illustrate an exemplary external headpiece 1400 that may be used in accordance with present systems and methods. The components shown in FIGS. 15A-15C are merely illustrative of the many different components that may be included within headpiece 1400. Additional or alternative components may be included within headpiece 1400 as may serve a particular application.

FIG. 15A is an exploded perspective view of the exemplary external headpiece 1400 showing various components of the external headpiece 1400. FIG. 15A is a perspective view of the exemplary external headpiece 1400 shown without a headpiece cover. FIG. 15C is cross-sectional side view of the exemplary external headpiece 1400 shown without a headpiece cover. As shown in FIGS. 15A-15C, the external headpiece 1400 may include a headpiece cover 1500 in which a headpiece cavity 1502 is defined. The external headpiece 1400 may additionally include a headpiece base 1504 that may be attached to the headpiece cover 1500. Components in the external headpiece 1400 may be housed in the headpiece cavity 1502 such that they are substantially surrounded by headpiece cover 1500 and the headpiece base 1504.

The external headpiece 1400 may include a circuit board 1506 (e.g., a printed circuit board) having electronic circuitry 1508 disposed thereon. The electronic circuitry 1508 may be disposed on any suitable portions of the circuit board 1506. A bottom surface 1510 of the circuit board 1506 may face generally towards the headpiece base 1504. The electronic circuitry 1508 may include the sound processor 1106 or at least a portion of the sound processor 1106. The electronic circuitry 1508 may be configured to direct the implantable cochlear stimulator 1110 to generate and apply electrical stimulation to one or more stimulation sites within the cochlea 1300 of a patient by transmitting control parameters (including, but not limited to, stimulation parameters) to the implantable cochlear stimulator 1110 via communications link 1118. The electronic circuitry 1508 may additionally or alternatively be configured to transmit power to the implantable cochlear stimulator 1110 and may be configured to receive data from the cochlear stimulator 1110.

The external headpiece 1400 may further include an induction coil 1512 disposed below the bottom surface 1510 of the circuit board 1506. The induction coil 1512 may include a metallic wire or tube wound in a coiled configuration. In some examples, the induction coil 1512 may include a coiled wire arranged in a generally disc-shaped and/or annular-shaped holder. It will be recognized that the induction coil 1512 may have any suitable size and shape as may serve a particular application.

The induction coil 1512 may have a top surface 1514 and an interior radial surface 1516, as illustrated in FIG. 15A. The induction coil 1512 may be seated in the headpiece base 1504. Accordingly, the induction coil 1512 may be in close proximity to the head 1402 of the patient when the headpiece base 1504 is adjacent to the head 1402.

In some examples, the external headpiece 1400 may additionally include a telemetry flux guide 1518 positioned or disposed between the circuit board 1506 and the induction coil 1512. The telemetry flux guide 1518 may have a generally annular shape with an inner radial surface 1520 defining an aperture extending through a central portion of the telemetry flux guide 1518. The telemetry flux guide may be adjacent to the bottom surface 1510 of the circuit board 1506 and the top surface 1514 of the induction coil 1512.

The telemetry flux guide 1518 may include any material suitable for directing magnetic flux away from the circuit board 1506. For example, the telemetry flux guide 1518 may include a material having a relatively high resistivity that provides a low reluctance path for magnetic flux of the telemetry magnetic field. Additionally, the telemetry flux guide 1518 may include a powdered material, such as a powdered metallic material having a relatively small particle size, in order to prevent the generation of eddy current in the telemetry flux guide 1518. For example, eddy currents might be generated in a solid conductive material (as opposed to a powdered conductive material) in the presence of the telemetry magnetic field since the telemetry magnetic field is a changing magnetic field generated by an alternating current passing through the induction coil 1512.

The powdered material in telemetry flux guide 1518 may be held together using any suitable material, such as a polymer material. In some examples, the powdered metallic material may include iron and/or other ferrite materials. Additionally, the telemetry flux guide 1518 may be suitable for frequencies of telemetry signals generated and/or received by the induction coil 1512, such as, for example, an approximately 49 MHz telemetry signal and/or an approximately 10.7 MHz telemetry signal. A telemetry flux guide 1518 including a material having a relative permeability (i.e., the ratio of the permeability of the alloy to the permeability of free-space) of approximately 9 may be suitable for a frequency range that includes 49 MHz and 10.7 MHz telemetry signals. However, it will be recognized that the telemetry flux guide 1518 may have any other suitable relative permeability value as may serve a particular application. Additionally or alternatively, telemetry flux guide 1518 may have a relatively high resistivity and a relatively small particle size in order to facilitate redirection of magnetic flux while minimizing the generation of eddy currents in the telemetry flux guide 1518.

The telemetry flux guide 1518 may be positioned and configured to direct magnetic flux of the magnetic field generated by the induction coil 1512 away from the circuit board 1506, as will be described in greater detail below. For example, a telemetry magnetic field may generated by the induction coil 1512 to transmit a telemetry signal. Magnetic flux of the telemetry magnetic field may be directed away from the circuit board 1506 by the telemetry flux guide 1518, thereby protecting the electronic circuitry 1508 on the circuit board 1506 from the telemetry magnetic field. By directing the magnetic flux in the telemetry magnetic field away from the circuit board 1506, energy losses from the induction coil 1512 to the electronic circuitry 1508 via the telemetry magnetic field may be minimized, thereby extending the life of batteries used to provide power to one or more components of the cochlear implant system 1100.

In some examples, the external headpiece 1400 may additionally or alternatively include a retention magnet 1522 disposed between the circuit board 1506 and the headpiece base 1504. The retention magnet 1522 may have a top surface 1524 generally facing the bottom surface 1510 of the circuit board 1506. The retention magnet 1522 may additionally have an outer radial surface 1526. In some embodiments, the retention magnet 1522 may be positioned in the external headpiece 1400 such that the retention magnet 1522 is at least partially surrounded by the induction coil 1512 and/or the telemetry flux guide 1518. Accordingly, the outer radial surface 1526 of the retention magnet 1522 may generally face the inner radial surface 1516 of the induction coil 1512 and/or the inner radial surface 1520 of the telemetry flux guide 1518. For example, the retention magnet 1522 may be positioned in an aperture defined by the inner radial surface 1520 extending through the telemetry flux guide 1518.

The retention magnet 1522 may be configured to produce a retention magnetic field for securing one or more components of a cochlear implant system 1100 to a head 1402 of a patient. For example, the retention magnet 1522 may be disposed adjacent to the headpiece base 1504 such that the retention magnet 1522 is in close proximity to the head 1402 of the patient when the headpiece base 1504 is adjacent to the head 1402. A portion of the cochlear stimulation portion 1104 of the cochlear implant system 1100, such as the receiver 1408 shown in FIG. 14, may similarly include a magnet configured to magnetically couple with the retention magnet 1522. Accordingly, when the headpiece base 1504 is positioned adjacent to the head 1402 of the patient near the receiver 1408, the retention magnet 1522 may be magnetically coupled to the magnet of the cochlear stimulation portion 1104, thereby securing and/or orienting the external headpiece 1400 on the head 1402.

The external headpiece 1400 may additionally or alternatively include a retention flux guide 1528 positioned between the circuit board 1506 and the retention magnet 1522. The retention flux guide 1528 may at least partially surround the retention magnet 1522. As illustrated in FIGS. 15A and 15C, a top wall 1530 of the retention flux guide 1528 may be disposed in between and adjacent to the bottom surface 1510 of the circuit board 1506 and the top surface 1524 of the retention magnet 1522. Additionally, a side wall 1532 of the retention flux guide 1528 may at least partially surround the outer radial surface 1526 of the retention magnet 1522. The side wall 1532 of the retention flux guide 1528 may be adjacent to the outer radial surface 1526 of the retention magnet 1522, the inner radial surface 1516 of the induction coil 1512, and/or the inner radial surface 1520 of the telemetry flux guide 1518.

The retention flux guide 1528 may include any material suitable for redirecting magnetic flux associated with a magnetic field produced by the retention magnet 1522. For example, the retention flux guide 1528 may include a material having a relatively high permeability. In some examples, the retention flux guide 1528 may include a metallic material, such as a mu-metal alloy comprising nickel and iron. A relatively high permeability mu-metal alloy may have a relative permeability between approximately 60,000 and 300,000. For example, a mu-metal alloy may have a relative permeability of approximately 100,000. A high-permeability mu-metal alloy may include any suitable ratio of nickel and iron, such as, for example, a ratio of approximately 80% nickel and 20% iron. It will be recognized that the retention flux guide 1528 may alternatively include any suitable material having any suitable relative permeability.

The retention flux guide 1528 may be configured to direct magnetic flux of a retention magnetic field surrounding the retention magnet 1522 away from the circuit board 1506 and/or away from the telemetry flux guide 1518. Accordingly, magnetic flux from the retention magnet 1522 may be directed away from the circuit board 1506, thereby protecting the electronic circuitry 1508 on the circuit board 1506 from the retention magnetic field.

As mentioned, the retention flux guide 1528 may also direct magnetic flux of the retention magnetic field away from the telemetry flux guide 1518, thereby preventing saturation of powdered metallic material in the telemetry flux guide 1518 with magnetic flux from the retention magnet. Magnetic flux from the retention magnet 1522 may significantly reduce the relative permeability of the powdered metallic material in the telemetry flux guide 1518, reducing the effectiveness of the telemetry flux guide 1518 in directing magnetic flux from the induction coil 1512 away from the circuit board 1506. Accordingly, the retention flux guide 1528 may direct magnetic flux of the retention magnetic field away from the telemetry flux guide 1518, thereby preventing magnetic flux from saturating the telemetry flux guide 1518.

By directing magnetic flux away from the electronic circuitry 1508 in the circuit board 1506, the telemetry flux guide 1518 and/or the retention flux guide 1528 may enable the induction coil 1512 and/or the retention magnet 1522 to be located within the external headpiece 1400 in relatively close proximity to the circuit board 1506. Accordingly, the sound processor portion 1102 of the cochlear implant system 1100 may be made more compact by consolidating electronic and magnetic field emitting components within the headpiece as illustrated in FIGS. 15A-15C. This may increase the ease of use and comfort for a patient using the cochlear implant system 1100 in comparison to conventional cochlear implant systems in which electronic circuitry is separated from the headpiece. For example, a consolidated unit, such as that illustrated in FIGS. 15A-15C, may eliminate the need for a separate behind-the-ear unit. Hence, the unit illustrated in FIGS. 15A-15C may be referred to as a "one piece system headpiece".

In some embodiments, the cochlear stimulation portion 1104 of a cochlear implant system 1100 may additionally or alternatively include a retention flux guide and/or a telemetry flux guide for directing magnetic flux away from electronic components in the cochlear stimulation portion 1104. For example, a receiver 1408 in the cochlear stimulation portion 1104 may include an induction coil and/or a retention magnet, similar to the external headpiece 1400 as described above. A retention flux guide and/or a telemetry flux guide may be included in the receiver 1408 to redirect magnetic flux away from electronic circuitry that may be located in close proximity to the induction coil and/or the retention magnet.

Additionally, as illustrated in FIGS. 15B and 15C, the external headpiece 1400 may include one or more batteries 1534 to power the sound processor portion 1102 and/or the cochlear stimulation portion 1102 of the cochlear implant system 1100. Batteries 1534 may be disposed within the headpiece cover cavity 1502 of the headpiece cover 1500 and may be located adjacent circuit board 1506. In some embodiments, batteries 1534 may be located outside of the external headpiece 1400.

Figure 16:
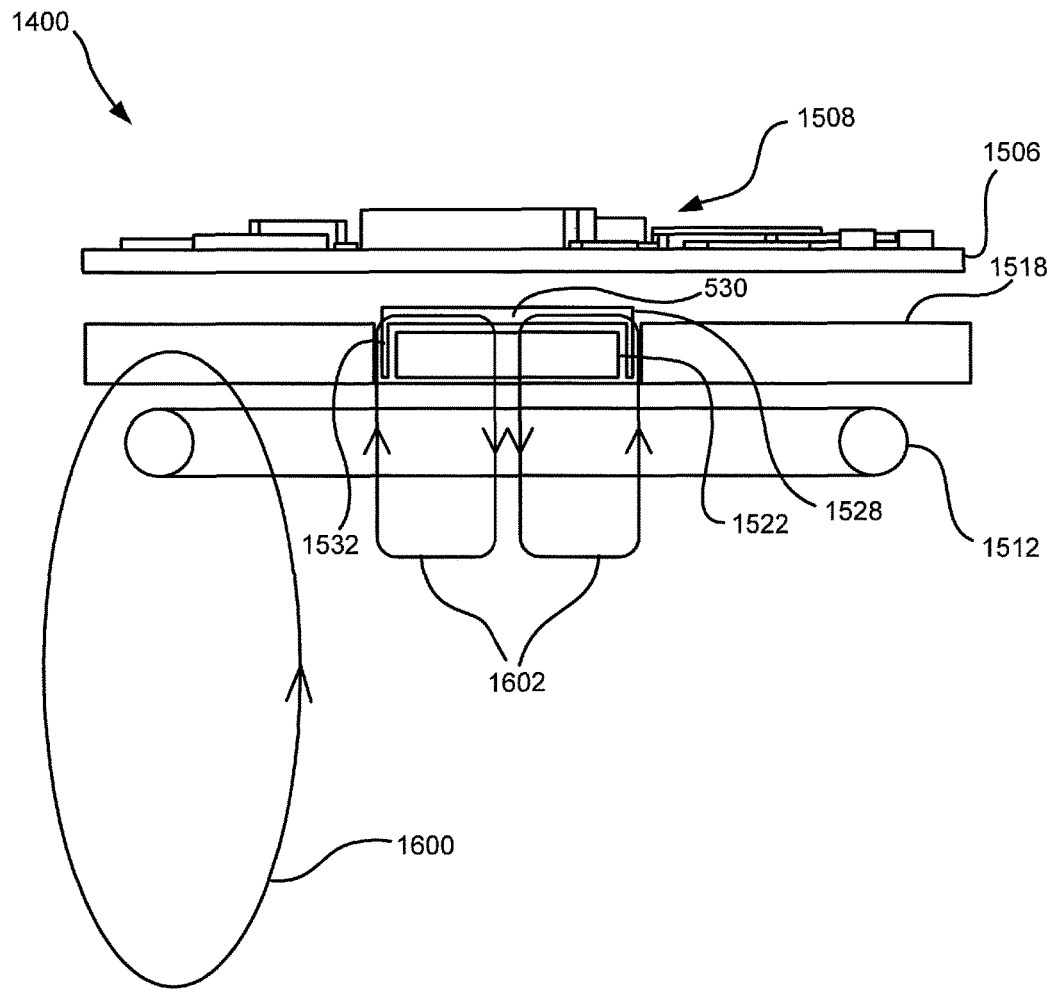
FIG. 16 illustrates magnetic flux surrounding an induction coil and a retention magnet in an exemplary external headpiece according to principles described herein.

FIG. 16 illustrates magnetic flux surrounding an induction coil 1512 and a retention magnet 1522 in an exemplary external headpiece 1400 in accordance with the present systems and methods. As illustrated in FIG. 16, magnetic flux 1600 may surround the induction coil 1512. The magnetic flux 1600 is represented as a flux path surrounding the induction coil 1512. Additionally, magnetic flux 1602 may pass through and surround retention magnet 1522. The magnetic flux 1602 is represented as flux paths surrounding and passing through the retention magnet 1522. It will be recognized that additional flux paths other than those illustrated in FIG. 16 may be associated with the telemetry magnetic field surrounding the induction coil 1512 and the retention magnetic field surrounding the retention magnet 1522.

The telemetry flux guide 1518 may provide a low reluctance path for the magnetic flux 1600 surrounding the induction coil 1512. As illustrated in FIG. 16, the path of the magnetic flux 1600 may be directed through the telemetry flux guide 1518 such that a path of the magnetic flux 1600 between the induction coil 1512 and the circuit board 1506 may be shortened. The magnetic flux 1600 of the telemetry magnetic flux field surrounding the induction coil 1512 may therefore be redirected by the telemetry flux guide 1518 such that the magnetic flux 1600 is substantially prevented from reaching the circuit board 1506, thereby reducing or eliminating magnetic flux passing through the electronic circuitry 1508.

The retention flux guide 1528 may provide a high permeability path for the magnetic flux 1602 surrounding and passing through the retention magnet 1522. As illustrated in FIG. 16, the path of the magnetic flux 1602 may be directed through the retention flux guide 1528 such that a path of the magnetic flux 1602 passes generally through and/or along the top wall 1530 and/or the side wall 1532 of the retention flux guide 1528. Accordingly, a path of the magnetic flux 1602 between the induction coil 1512 and the circuit board 1506 may be shortened. Similarly, a path of the magnetic flux 1602 between the retention magnet 1522 and the telemetry flux guide 1518 may be shortened. The magnetic flux 1602 of the retention magnetic flux field surrounding and passing through the retention magnet 1522 may therefore be redirected by the retention flux guide 1528 such that the magnetic flux 1602 is substantially prevented from reaching the circuit board 1506 and/or the telemetry flux guide 1518, thereby reducing or eliminating magnetic flux from the retention magnet passing through the electronic circuitry 1508 and/or the telemetry flux guide 1518.

The preceding description has been presented only to illustrate and describe embodiments and examples of the principles described. This description is not intended to be exhaustive or to limit these principles to any precise form disclosed. Many modifications and variations are possible in light of the above teaching.

What is claimed is:

1. A headpiece for use with a cochlear implant, comprising:
    a headpiece housing;
    a circuit board within the housing;
    a retention magnet within the headpiece housing that generates a retention magnetic field, the retention magnet including a bottom surface that faces the cochlear implant, a top surface that is opposite the bottom surface and that faces and is aligned with a portion the circuit board, and an outer radial surface between the top and bottom surfaces;

an induction coil within the headpiece housing that transmits audio signals to the cochlear implant by generating a telemetry magnetic field; and a retention flux guide located within the headpiece housing and adjacent to the top surface of the retention magnet such that at least a portion of the retention flux guide is located between the top surface of the retention magnet and the portion of the circuit board that is aligned with the top surface of the retention magnet.

2. A headpiece as claimed in claim 1, wherein
the retention flux guide at least partially surrounds the outer radial surface of the retention magnet.

3. A headpiece as claimed in claim 1, wherein
the retention flux guide extends radially beyond the outer radial surface of the retention magnet.

4. A headpiece as claimed in claim 1, wherein
the retention flux guide is formed from a mu-metal alloy.

5. A headpiece as claimed in claim 1, wherein
the retention flux guide is formed from a mu-metal alloy having a relative permeability between approximately 60,000 and 300,000.

6. A headpiece for use with a cochlear implant, comprising:
a headpiece housing;
a retention magnet within the headpiece housing that generates a retention magnetic field, the retention magnet including a bottom surface that faces the cochlear implant, a top surface opposite the bottom surface, and an outer radial surface between the top and bottom surfaces;
an induction coil within the headpiece housing that transmits audio signals to the cochlear implant by generating a telemetry magnetic field; and
a retention flux guide, formed from a material having a relatively high permeability, positioned within the headpiece housing and adjacent to the top surface of the retention magnet such that retention flux is directed inwardly of the induction coil.

7. A headpiece as claimed in claim 1, wherein
the retention flux guide is in contact with the retention magnet.

8. A headpiece as claimed in claim 1, wherein
the headpiece housing includes a base and a cover.

9. A headpiece as claimed in claim 8, wherein
the induction coil is seated on the base.

10. A headpiece as claimed in claim 1, further comprising:
a telemetry flux guide within the headpiece.

11. A headpiece as claimed in claim 1, further comprising:
a microphone within the headpiece housing; and
signal processing electronics on the circuit board and operably connected to the microphone and to the induction coil.

12. A headpiece as claimed in claim 11, further comprising:
a power source within the headpiece housing.

13. A headpiece as claimed in claim 11, wherein
the retention flux guide is between the retention magnet and the signal processing electronics.

14. A headpiece for use with a cochlear implant, comprising:
a headpiece housing;
a retention magnet within the headpiece housing that generates a retention magnetic field, the retention magnet including a bottom surface that faces the cochlear implant, a top surface opposite the bottom surface, and an outer radial surface between the top and bottom surfaces;
means, within the headpiece housing, for transmitting audio signals to the cochlear implant; and
a retention flux guide within the headpiece housing that extends over the top surface of the retention magnet and that directs retention flux away from the means for transmitting audio signals.

15. A headpiece as claimed in claim 14, wherein
the retention flux guide at least partially surrounds the outer radial surface of the retention magnet.

16. A headpiece as claimed in claim 14, wherein
the retention flux guide extends radially beyond the outer radial surface of the retention magnet.

17. A headpiece as claimed in claim 14, wherein
the retention flux guide is formed from a mu-metal alloy.

18. A headpiece as claimed in claim 14, wherein
the retention flux guide is formed from a mu-metal alloy having a relative permeability between approximately 60,000 and 300,000.

19. A headpiece as claimed in claim 14, wherein
the retention flux guide is formed from a material having a relatively high permeability.

20. A headpiece as claimed in claim 14, wherein
the retention flux guide is in contact with the retention magnet.

21. A headpiece as claimed in claim 14, wherein
the headpiece housing includes a base and a cover.

22. A headpiece as claimed in claim 21, wherein
the induction coil is seated on the base.

23. A headpiece as claimed in claim 14, further comprising:
a microphone within the headpiece housing; and
signal processing electronics within the headpiece housing and operably connected to the microphone and to the induction coil.

24. A headpiece as claimed in claim 23, further comprising:
a power source within the headpiece housing.

25. A headpiece as claimed in claim 23, wherein
the retention flux guide is between the retention magnet and the signal processing electronics.

26. A headpiece as claimed in claim 1, wherein
the induction coil defines an inner perimeter; and
the retention flux guide defines an outer perimeter that is no greater than the inner perimeter of the induction coil.

* * * * *